United States Patent
DiNovo et al.

(10) Patent No.: US 9,944,920 B2
(45) Date of Patent: *Apr. 17, 2018

(54) BIODEGRADABLE IMMOBILIZED ENZYMES AND METHODS OF MAKING THE SAME

(71) Applicant: Guild Associates, Inc., Dublin, OH (US)

(72) Inventors: Augustine A. DiNovo, Charleston, SC (US); Dominic P. DiNovo, Dublin, OH (US); David A. Schofield, Hollywood, SC (US); Matthew F. Smiechowski, Westerville, OH (US); Francis H. Verhoff, Cincinnati, OH (US)

(73) Assignee: Guild Associates, Inc., Dublin, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/675,659

(22) Filed: Nov. 13, 2012

(65) Prior Publication Data

US 2013/0309746 A1 Nov. 21, 2013

Related U.S. Application Data

(60) Provisional application No. 61/558,758, filed on Nov. 11, 2011.

(51) Int. Cl.
| | |
|---|---|
| *C12N 11/10* | (2006.01) |
| *C12N 11/12* | (2006.01) |
| *C12N 11/02* | (2006.01) |
| *C12N 11/06* | (2006.01) |

(52) U.S. Cl.
CPC .............. *C12N 11/10* (2013.01); *C12N 11/02* (2013.01); *C12N 11/06* (2013.01); *C12N 11/12* (2013.01)

(58) Field of Classification Search
None
See application file for complete search history.

(56) References Cited

U.S. PATENT DOCUMENTS

| | | | | | |
|---|---|---|---|---|---|
| 5,916,789 | A | * | 6/1999 | Webbers et al. | 435/178 |
| 2006/0286006 | A1 | * | 12/2006 | McDaniel et al. | 422/129 |

FOREIGN PATENT DOCUMENTS

RU 2261911 C1 * 10/2005

OTHER PUBLICATIONS

Khan, A.A., and Alzohairy, M.A. "Recent Advances and Applications of Immobilized Enzyme Technologies: A Review", Research Journal of Biological Sciences 2010, vol. 5, pp. 565-575.*
Park, H.J., Uhm, K.-N., and Kim, H.-K., "Biotransformation of Amides to Acids Using a Co-Cross-Linked Enzyme Aggregate of Rhodococcus erythropolis Amidase", Journal of Microbiology and Biotechnology 2010, vol. 20, pp. 325-331.*
Chen, P.-H., Kuo, T.-Y., Liu, F.-H., Hwang, Y.-H., Ho, M.-H., Wang, D.-M., Lai, J.-Y., and Hsieh, H.-J. "Use of Dicarboxylic Acids to Improve and Diversify the Material Properties of Porous Chitosan Membranes", Journal of Agricultural and Food Chemistry 2008, vol. 56, pp. 9015-9021.*
Vaidya, B.K., and Singhal, R.S. "Use of insoluble yeast beta-glucan as a support for immobilization of Candida rugosa lipase", Colloids and Surfaces B: Biointerfaces 2008, vol. 61, pp. 101-105.*
Kay et al., "Coupling of Enzymes to Cellulose using Chloro-s-triazines", Nature 1967, vol. 216, pp. 514-515.*

* cited by examiner

*Primary Examiner* — Michelle F. Paguio Frising
(74) *Attorney, Agent, or Firm* — Edward E. Sowers; Brannon Sowers & Cracraft PC

(57) ABSTRACT

The present application discloses immobilized enzymes and immobilized enzyme materials comprising a crosslinked enzyme having a support material which includes a biomass material different than the biomass used to initially derive the enzyme. Optionally, the immobilized enzyme further includes a polymeric material and/or the biomass which was used to initially derive the enzyme. The resulting immobilized enzyme materials may be biodegradable. The present application also discloses methods of making and using the disclosed immobilized enzyme materials.

29 Claims, 16 Drawing Sheets

BIODEGRADABLE IMMOBILIZED ENZYMES AND METHODS OF MAKING THE SAME

CROSS REFERENCE TO RELATED APPLICATIONS

This application is related to and claims priority to U.S. Provisional Patent Application No. 61/558,758 filed on Nov. 11, 2011.

FIELD

The claimed technology relates generally to biocatalysts such as enzymes and more specifically to the immobilization of enzymes.

BACKGROUND

Immobilized biocatalysts have found applications in a variety of industries where specific chemical conversions are required. Specific large scale examples in the food and pharmaceutical industries include immobilized glucose isomerase for the conversion of glucose to fructose and immobilized penicillin acylase for the preparation of derivatives of penicillin. Immobilized enzymes can be used for large scale bioremediation such as the destruction of undesirable chemical compounds. Another application involves small scale immobilized enzymes used in diagnostic reactions wherein the biocatalyst facilitates a chemical reaction which produces a detectable chemical moiety or other chemical change. More applications for immobilized enzymes will likely be developed in the future.

Immobilized biocatalysts (enzymes) provide advantages over bio catalysts in solution such as those provided in a liquid form or in a dry form to be dissolved in a liquid. Immobilized enzymes can be easily separated from the solution and thus permit the reuse of these enzymes hence reducing the cost of the enzyme in the production of a product. In the two cases cited above, immobilized enzymes are used in a packed column with the reactant solution pumped through the column and the desired chemical conversion accomplished when the solution leaves the column. In this process, the enzymes are used multiple times at high concentrations to achieve efficient usage of the enzymes.

In addition to ease of separation, immobilized enzymes can provide other potential advantages including greater thermal stability, pH stability, and the like during storage as well as during usage. Immobilized biocatalysts also can provide greater activity in various solvents compared to the enzymes in solution. There are often advantages to the physical form because immobilized biocatalysts can be provided in a granular form which reduces dust and improves handling of the product. As with a dried enzyme, the activity of the immobilized enzyme per mass of material can be varied as desired for a particular application.

An immobilized enzyme may be composed of the enzyme material combined with a solid matrix to which the enzyme is attached or held by chemical or physical means. The enzyme may be attached to the surface of the matrix, or if the matrix is porous enough to permit diffusion of the substrate, the enzyme may be distributed throughout the matrix. There are many methods proposed for the immobilization of biocatalysts including the entrapment of the enzyme in gel, the covalent, hydrophobic, electrostatic, and other methods for attachment of the enzyme to an inorganic or organic solid. The cross linking of the enzyme with whole cells, enzyme crystals, etc may be accomplished using reagents such as glutaraldehyde (GA) and polyethylenimine (PEI).

The conversion of a biocatalyst to an immobilized form may require more processing and hence may increase the cost of production for that enzyme form. Any increased cost must be compensated by increased productivity, shelf life, use in solvents, or some other advantage. Therefore, the cost of immobilization is an important consideration in the production of an immobilized enzyme. A lower cost for immobilization hence provides for a more economical usage of the immobilized enzyme.

Of the methods proposed for the immobilization of the enzymes, the use of cross linking whole cells is one of the most cost-effective. This method utilizes the whole cells are those of the microorganism used to make the enzyme and hence are available for no cost or even a negative cost if there is a cost associated with the disposal of the cell mass.

Various immobilization processes have been suggested for enzymes including attachment to silica supports. This process involves the fermentation of microorganism for the production of the enzyme, the separation (or purification) of the enzyme from the biomass, the chemical attachment or encapsulation of the enzyme to the matrix, and the production of the final product form. These immobilizations have the disadvantage of incurring the cost of the matrix to which the enzyme is attached. Further the separation of the enzyme from the fermentation biomass involves some loss of enzyme and enzyme activity, as well as associated purification processing costs. These disadvantages are overcome by the immobilization of the enzyme directly with the biomass used to produce the enzyme.

Some enzyme substrates have limited solubility in water and have better solubility in organic solvents or mixtures of organic solvents and water. For example, due to these properties, organic solvent solutions are often used to wash away organophosphorus compounds or organic solvents are used in the processing of triglycerides. Soluble enzymes are often deactivated or rendered inert in organic solvents or mixtures; however, immobilized enzymes can maintain some activity in solvents compared to soluble enzymes. Hence immobilized enzymes have the capacity to react with the higher concentrations of their substrates in such solvents.

Application of immobilized enzymes may require the disposal of the enzyme after usage. For example, the immobilized enzyme used in a column reactor would require disposal after use. Also, some immobilized enzymes can be considered for use directly in the environment. For example, immobilized OPH enzyme could be dispersed on an agricultural field for decontaminating a pesticide or other organophosphorus compound.

SUMMARY

The claimed technology is set forth in the claims below, and the following is not in any way to limit, define or otherwise establish the scope of legal protection. In general terms, the disclosed technology relates to immobilized enzymes and methods of producing the same.

One aspect of the disclosed technology provides a range of immobilized enzymes that utilize one or more biomass materials as components of a support matrix. The disclosed technology therefore minimizes cost and simplifies production. Advantageously, such immobilized enzymes are stable and able to operate over a range of conditions, in particular in the presence of a range of solvents, over a range of pH values, and at the temperatures encountered in the field. The immobilized enzymes and immobilized enzyme materials are, in some instances, also biodegradable. Specific immobilized enzymes are provided which are able to transform organophosphates and related toxic materials into less harmful/harmless materials and optionally these are capable of biodegradation to further effect and simplify remediation efforts. Methods for the preparation and utilization of these immobilized enzymes are also provided.

In general, the disclosed technology provides an immobilized enzyme material. The material may be an immobilized organophosphate-degrading enzyme material. The enzyme material may comprise a crosslinked enzyme having a support matrix that includes a biomass material. The biomass material may be different from the biomass material the enzyme was derived from. The crosslinked enzyme may be formed by reacting the enzyme with at least two polyfunctional materials.

Enzymes that can be incorporated into the immobilized enzymes of the disclosed technology include, but are not limited to, enzymes from a class selected from the group consisting of Oxidoreductases, Transferases, Hydrolases, Lyases, Isomerases, and Ligases. Organophosphate-degrading enzymes such as organophosphate hydrolase (OPH), organophosphorus acid anhydrolase (OPAA), diisopropylfluorophosphatase (DFPase), and the like may be used. Enzymes such as lactase, glucose isomerase, peroxidase, alcohol dehydrogenase, xylanase, pyruvate decarboxylase, catalase, invertase, phytase, amyloglucosidase, glucose oxidase, penicillin acylase, and the like may also be mentioned. The immobilized enzymes of the disclosed technology may exhibit improved temperature stability compared to the free enzyme. Optionally, the disclosed technology may be adapted and applied to combinations of two or more enzymes.

The disclosed technology therefore provides the possibility of low cost enzyme products, where the enzyme may be organophosphate hydrolase and/or other enzymes. These products can be used for the destruction of organophosphorus compounds and for other chemical transformations. The disclosed technology provides an enzyme product that is stable in both storage and usage conditions. Further, the disclosed technology provides an enzyme product where the enzyme is active in solvents in which some organophosphorus compounds are more soluble or in which other chemical transformations can be brought about. In addition, the disclosed technology provides a range of immobilized enzyme products for organophosphorus decomposition as well as other enzyme applications that require the enzyme to be disposed of or left in the environment to decompose. These products are suitably biodegradable.

In the disclosed technology, the immobilized enzyme materials can function over a substantially broader pH range than the free enzyme, in the presence of a range of solvents, and at higher temperatures than the free enzyme.

The biomass material that is utilized in the support material may include biomass that is different from the biomass material the enzyme was derived from. In this regard it may include a combination of biomass that is different from the biomass material the enzyme was derived from and biomass that is the same as the biomass material the enzyme was derived from thereof, provided at least some of the biomass is different from the biomass the enzyme was derived from.

There are benefits in using biomass that is different from the biomass the enzyme was derived from. In this regard, one advantage is that the biomass that is different from the biomass the enzyme was derived from may be a waste product that otherwise would need to have been disposed of. Another advantage is that the characteristics of that biomass can be selected depending on the intended use of the immobilized enzyme. For example, the immobilized enzyme can be made biodegradable. This is useful when the immobilized enzyme is used to clean up environmental mishaps, including some forms of pesticides and chemical warfare agents, and in manufacturing applications where later disposal of the immobilized enzyme becomes necessary. For example, treatment of a field contaminated with an organophosphate pesticide can be decontaminated by applying a biodegradable form of the immobilized enzyme over the field's surface. Once the degradation is complete, the biodegradable immobilized enzyme simply degrades over time, making further clean-up/removal unnecessary.

In some examples, the physical properties of the final immobilized enzyme material can be modified through the choice of biomass. For example, the material can be made more or less rigid to enhance its suitability for a variety of reactor configurations. A more rigid particle would be advantageous in a packed bed reactor configuration. Similarly, immobilized enzyme material properties such as porosity, hydrophobicity, and solubility may be modified through the selection of biomass material to suit specific reaction conditions. In general, incorporating additional biomass, different from that which the enzymes was derived, provides additional options for specifically adapting the immobilized enzyme material compared to whole cell immobilizations that are limited to the properties of the biomass from which the enzyme was derived.

Suitable support materials may have a plurality of amine groups or other functional groups capable of reacting with the crosslinking material. Support materials can include one or more biomass materials, such a chitin, *Aspergillus niger* cells, wool and the like. One type of suitable biomass materials has a plurality of functional groups capable of reacting with the crosslinking material. Biomass materials containing amino groups thereon, such as for example a polyamine, have been used. Examples of such suitable biomass support materials include, but are not limited to, *Aspergillus niger* cells, yeast cells, cellulose, dextran, starch agar, alginate, carrageenans, collagen, gelatin, albumin, and ferritin. Other biomass materials such as cotton and wool can optionally be included, provided at least some support material having a plurality of functional groups is provided to support crosslinking. Support materials may also include synthetic and/or polymeric materials such as polyethylenimine, chitosan, polypyrrole, or other suitable material. Optionally, the support material may comprise a combination of one or more biomass materials and/or one or more polymeric support materials. Suitable polymeric support materials can include polyamines, such as for example polyethylenimine, polypyrrole, a protein, gelatin, and the like. In general, suitable biomass materials can include biomass materials generally free of functional groups and minimally involved in the crosslinked structure, biomass materials having a plurality of functional groups that are involved with the necessary crosslinking, and combinations thereof.

Suitable crosslinking materials include polyfunctional groups capable of reacting with the support material. Suitable crosslinking materials may also include polyfunctional groups capable of reacting with the support material, such as, for example, glutaraldehyde, di-aldehyde, an organic di-acid, disuccinimidyl suberate, dimethyl pimelimidate, dimethyl adipimidate, cyanuric chloride, succinic acid, hexamethylene diisocyanate, and the like. Other reagents capable of crosslinking to amines may also be contemplated.

Immobilized enzymes that utilize a biomass material for the support matrix are optionally biodegradable. In other examples, the biomass material is insoluble. The immobilized enzymes of the disclosed technology may therefore be biodegradable. Suitable biodegradable support materials include, but are not limited to, processed or unprocessed exoskeleton (mineral or organic), bone, chitin (soluble or insoluble), *Aspergillus niger* cells and the like.

In applications where the immobilized enzyme is applied over a large area open to the environment it can be advantageous for the immobilized enzyme to be biodegradable. Thus, the embodiments of the disclosed technology where the immobilized enzyme is biodegradable has utility for a variety of enzymes requiring disposal or enzymes that are dispersed in the environment.

The immobilized enzyme material can additionally include a solvent. This may be a solvent adapted to dissolve the material sought to be transformed. Solvents can include, but are not limited to, hexane, toluene, methanol, dimethyl sulfoxide, and the like. The immobilized enzymes may exhibit improved temperature stability compared to the free enzyme.

In general, the disclosed technology also provides a method for preparing such an immobilized enzyme material. In one example, the method includes the steps of providing an enzyme, a support material and a crosslinking material, and combining the support material and the crosslinking material with an aqueous suspension of the enzyme. The materials may be combined in any order; in some instances, the support material is added before the crosslinking material, whereas in other instances, the crosslinking material is added before the support material, in order to maximize activity. The step of combining the materials may suitably result in a flocculated product. The product can be used directly or isolated, dried, and formulated into particles having a desirable size and shape, depending on the intended application. The support material may include a biomass support material. Support materials other than biomass support materials can additionally be provided and added to the aqueous suspension of the enzyme. Optionally, the crosslinking material may be provided in a suitable solvent, such as water, alcohol, DMSO, and the like.

The immobilized enzyme material thus formed may be subjected to elevated temperatures. Subjecting the immobilized enzyme to elevated temperatures has generally increased the activity of the immobilized enzymes compared to a similar immobilized enzyme not subject to a treatment at elevated temperatures.

In general, the disclosed technology also provides a method for utilizing the immobilized enzyme material to transform a material susceptible to enzymatic transformation. The immobilized enzyme material may be provided in biodegradable form. In one example, the method involves providing the immobilized enzyme material, wherein the enzyme is in a form suitable for contacting the material susceptible to enzymatic transformation and adapted to effect the desired transformation, and contacting the immobilized enzyme material with the material susceptible to enzymatic transformation. In some examples such contacting involves dissolving the material susceptible to enzymatic transformation in a solvent to form a solution, and contacting the immobilized enzyme material with the solution. In applications involving environmental remediation, contacting can involve dispersing the immobilized enzyme material over the soil and depending on moisture in the soil to act as a solvent to dissolve the material susceptible to enzymatic transformation. In other examples where the material susceptible to enzymatic transformation is not soluble in water or water is not available, a solvent may need to be supplied. In other examples, the desired transformations may be carried out in a column, a vessel, or other reactor in which the immobilized enzyme material and the material susceptible to enzymatic transformation are combined with a solvent in which the material susceptible to enzymatic transformation has at least some solubility. In some embodiments the transformation involves transforming or degrading a material, which may be selected from pesticides, chemical warfare agents, nerve agents, and the like, into less harmful/harmless moieties. In general, the transformation may be a decomposition to a less harmful/harmless moiety or may be a conversion to a desired chemical compound.

A first aspect of the present disclosure is to provide immobilized organophosphate-degrading enzymes. In one example, a crosslinked organophosphate-degrading enzyme (ODE) was demonstrated by organophosphate hydrolase (OPH) formed by reacting the OPH with a support material and a crosslinking material, although in other examples other ODE may be used. Suitable support materials optionally have a plurality of amine groups. Support materials can include biomass materials such as chitin, *Aspergillus niger* cells, wool and the like. In addition, support materials can be polyamines, such as polyethylenimine, polypyrrole, a protein, gelatin, and the like. Suitable crosslinking materials may include polyfunctional groups capable of reacting with the support material such as for example glutaraldehyde, disuccinimidyl suberate, dimethyl pimelimidate, and the like.

In a further example, the crosslinked OPH material can involve a support matrix that includes a biomass material. The biomass material can be the biomass material that was used to generate the OPH, another biomass material, or a combination thereof. Examples of suitable support materials that are biomass materials include, but are not limited to chitin, *Aspergillus niger* cells, wool and the like. Immobilized enzymes that utilize a biomass material for the support matrix and the support material are optionally biodegradable. In other examples, the biomass material is insoluble.

In still a further example, the crosslinked OPH material can additionally include a solvent, optionally a solvent having a solvent adapted to dissolve the material sought to be transformed. Solvents can include, but are not limited to hexane, toluene, methanol, dimethyl sulfoxide, and the like. The immobilized OPH enzymes may exhibit improved temperature stability compared to the free enzyme.

A further aspect of the present disclosure includes immobilized enzymes having a support matrix that includes a biomass material that is different from the one the enzyme was derived from. In one such example, the immobilized enzyme can be formed by reacting an enzyme with a support material and a crosslinking material where the support material includes a biomass material. Biomass material utilized can include biomass that is different from the biomass material the enzyme was derived from, the same, or a combination thereof, provided at least some of the biomass is different from the biomass the enzyme was derived from. One type of suitable biomass materials has a plurality of functional groups capable of reacting with the crosslinking material. Biomass materials containing amino groups thereon, such as for example a polyamine, have been used. Examples of such suitable biomass support materials include, but are not limited to *Aspergillus niger* cells, yeast cells, cellulose, dextran, starch agar, alginate, carrageenans, collagen, gelatin, albumin, and ferritin. Other biomass materials such as cotton and wool can optionally be included, provided at least some support material having a plurality of functional groups is provided to support crosslinking. Suitable support materials can also include polyamines, such as for example polyethylenimine, polypyrrole, a protein, gelatin, and the like. Suitable crosslinking materials may include polyfunctional groups capable of reacting with the support material. Crosslinking materials suitable for reacting with support materials containing amines may include glutaraldehyde, disuccinimidyl suberate, dimethyl pimelimidate, and the like. Some examples of enzymes that can be incorporated into these immobilized enzymes include enzymes from a class selected from the group consisting of Oxidoreductases, Transferases, Hydrolases, Lyases, Isomerases, and Ligases. The immobilized enzymes described above may exhibit improved temperature stability compared to the free enzyme.

A still further aspect of the present disclosure includes immobilized enzymes which are biodegradable. Such biodegradable enzymes include a crosslinked enzyme having a support matrix derived from a support material that includes a biomass and a crosslinking material. Suitable biomass support materials optionally have a plurality of functional groups capable of reacting with the crosslinking material. Some biomass materials containing amino groups thereon, such as for example a polyamine, have also been used. In other examples, the biomass material used is soluble or insoluble in water as desired. Still other examples of such suitable biomass support materials include, but are not limited to *Aspergillus niger* cells or other bacterial cellular materials, yeast cells or other fungal cellular materials, cellulose, dextran, starch agar, alginate, carrageenans, collagen, gelatin, albumin, and ferritin. Other biomass materials such as cotton and wool can optionally be included. Suitable crosslinking materials may optionally include polyfunctional groups capable of reacting with the support material. In other examples, crosslinking materials which are heterofunctional, that is they contain two or more different functional groups, may be used. Some crosslinking materials suitable for reacting with support materials containing amines include glutaraldehyde, disuccinimidyl suberate, dimethyl pimelimidate, and the like. Some enzymes that can be incorporated into these immobilized enzymes include enzymes from a class selected from the group consisting of Oxidoreductases, Transferases, Hydrolases, Lyases, Isomerases, and Ligases. The biodegradable immobilized enzymes may exhibit improved temperature stability compared to the free enzyme.

A still further aspect of the present disclosure involves a method for preparing an immobilized enzyme in which at least a portion of the support material is a biomass material. In one example, the method includes the steps of providing an enzyme, a biomass support material and a crosslinking material, adding the biomass support material and the crosslinking material to an aqueous suspension of the enzyme with agitation to form a flocculent. An aqueous suspension can include any suspension which includes at least some water. Biomass materials other than biomass support materials can additionally be provided and added to the aqueous suspension of the enzyme. Support materials can additionally include a polyamine selected from the group consisting of polyethylenimine, polypyrrole, polyethylenediamine; a polyethylenimine (such as, for example, polydiethylenetriamine, polytriethylenetetramine, polypentaethylenehexamine or polyhexamethylenediamine); polymethylenedicyclohexylamine; polymethylenedianiline; polytetraethylenepentamine; polyphenylenediamine, blends of two or more of these polyamine compounds, and the like. A further example includes a method for preparing a biodegradable immobilized enzyme which includes the step of providing one or more support materials and a crosslinking agent that are biodegradable. Suitable biodegradable support materials include, but are not limited to processed (by grinding, pulverizing, or other mechanical means) or unprocessed exoskeleton (mineral or organic), bone, chitin (soluble or insoluble), *Aspergillus niger* cells and the like. Suitable crosslinking materials include, but are not limited to glutaraldehyde, a di-aldehyde, an organic di-acid, disuccinimidyl suberate, and dimethyl pimelimidate, polyfunctional aldehydes, polyfunctional organic halides, polyfunctional anhydrides, polyfunctional azo compounds, polyfunctional isothiocyanates, polyfunctional isocyanates, blends of two or more of these amine reactive materials, succindialdehyde, terephthaldehyde, bis-diazobenzidine-2,2'-disulfonic acid, 4,4'-difluoro-3,3'-dinitrodiphenylsulfone, diphenyl-4,4'-dithiocyanate-2,2'-disulfonic acid, 3-methoxy-diphenylmethane-4,4'-diisocyanate, toluene-2-isocyanate-4-isothiocyanate, toluene-2,-4-diisothiocyanate, diazobenzidine, diazobenzidine-3,3'-dianisidine, N,N'-hexamethylene bisiodoacetamide, hexamethylene diisocyanate, cyanuric chloride, 1,5-difluoro-2,4-dinitrobenzene, blends or two or more of these amine reactive materials, and the like. Optionally, the crosslinking material may be provided in a suitable solvent such as water, alcohol, DMSO, and the like. The method can be utilized to form immobilized enzymes from a class selected from the group consisting of Oxidoreductases, Transferases, Hydrolases, Lyases, Isomerases, and Ligases. Subjecting the immobilized enzymes described above to elevated temperatures after isolation can increase the immobilized enzymes activity compared to a similar immobilized enzyme not subject to a treatment at elevated temperatures.

A still further aspect of the present disclosure involves a method for utilizing a biodegradable enzyme to transform a material susceptible to enzymatic transformation. In one such example, the method involves providing a biodegradable enzyme in a form suitable for contacting the material and adapted to effect the desired transformation, and contacting the biodegradable immobilized enzyme with the material susceptible to enzymatic transformation. Optionally such contacting involves dissolving the material susceptible to enzymatic transformation in a solvent to form a solution, and contacting the biodegradable immobilized enzyme with the solution. In applications involving environmental remediation, contacting can involve dispersing the biodegradable immobilized enzyme over the soil and depending on moisture in the soil to act as a solvent to dissolve the material susceptible to enzymatic transformation. In other examples where the material susceptible to enzymatic transformation is not soluble in water or water is not available, a solvent may be supplied.

In particular organophosphate compounds are potent neurotoxins commonly used as pesticides, insecticides, and as chemical warfare agents. Although organophosphate use as a chemical warfare agent has been restricted by international treaties; use of these compounds as agricultural and domestic pest controls present legitimate concerns about contamination of soil and water systems, along with remediation of contaminated facilities and containers. Many organophosphates can be decomposed with chemical decontaminants such as sodium hydroxide, potassium hydroxide, hypochlorite, and hydrogen peroxide or an area can be treated with detergent and water to remove the contamination. Although each of these methods is effective at treating contamination to an extent, there are also secondary issues that must be considered in the application. For example, several of these materials are corrosive in nature and all waste products from the treatments must still be handled as hazardous waste.

In order to retain the effectiveness of a chemical treatment and improve upon the waste handling aspects of a treatment process the utilization of Organophosphate Degrading Enzymes (ODE) for decontamination of organophosphates is considered. ODE is a general term to describe enzymes which are capable of catalyzing the hydrolysis of a wide range of organophosphate triesters and organophosphofluoridates. Aryldialkylphosphatases (E.C. 3.1.8.1) and diisopropyl-fluorophosphatase (E.C. 3.1.8.2) have been shown to be capable of cleaving P—O, P—F, P—S, P—CN bonds making them reactive against a wide variety of organophosphate pesticides such as: acephate, coumaphos, demeton, diazinon, dursban, malathion, paraoxon, parathion, methyl paraoxon, and methyl parathion; and chemical warefare agents including: sarin, soman, and VX.

In other examples, the desired transformations may be carried out in a column, a reaction bed, a vessel, or other reactor in which the biodegradable immobilized enzyme and the material susceptible to enzymatic transformation are combined with a solvent in which the material susceptible to enzymatic transformation has at least some solubility. In both of the above examples, the biodegradable immobilized enzymes can function over a substantially broader pH than the free enzyme, in the presence of a range of solvents, and at higher temperatures than the free enzyme. Examples of suitable solvents include, but are not limited to hexane, toluene, methanol, dimethyl sulfoxide, and the like.

Further objects, embodiments, forms, benefits, aspects, features and advantages of the disclosed technology may be obtained from the description, drawings, and claims provided herein.

DESCRIPTION

Figure 1:
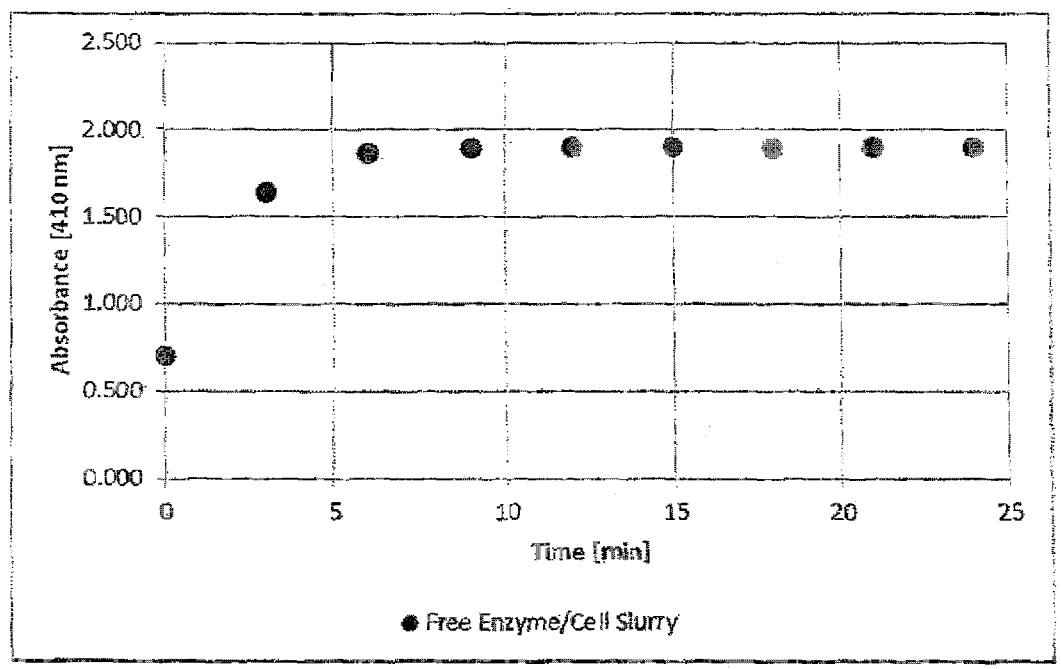
FIG. 1 is a graph showing absorbance vs. time data of OPH enzyme in cell slurry.

For the purposes of promoting an understanding of the principles of the disclosed technology and presenting its currently understood best mode of operation, reference will now be made to the embodiments illustrated in the drawings and specific language will be used to describe the same. It will nevertheless be understood that no limitation of the scope of the disclosed technology is thereby intended, with such alterations and further modifications in the illustrated device and such further applications of the principles of the disclosed technology as illustrated therein being contemplated as would normally occur to one skilled in the art to which the disclosed technology relates.

The disclosed technology addresses the problem of providing: (a) immobilized enzymes capable of promoting a range of desirable transformations that have a support matrix that includes a biomass material; (b) methods for the preparing these immobilized enzymes, and (c) methods for utilizing the immobilized enzymes. The immobilized enzymes of this disclosure have reduced material costs, good thermal stability, good activity in the presence of a range of solvents, and over a wide range of pH's, and can be produced to exhibit biodegradability. Suitable biomass materials can include biomass materials generally free of functional groups and minimally involved in the crosslinked structure, biomass materials having a plurality of functional groups that are involved with the necessary crosslinking, and combinations thereof. One example involves a crosslinked immobilized enzyme that includes organophosphate hydrolase, and is capable of transforming or degrading a range of pesticides, nerve agents, and the like into less harmful/harmless moieties. Forms of the immobilized organophosphate hydrolase can be biodegradable.

The general methods for preparing the immobilized enzymes of this present disclosure involve providing the enzyme, the biomass material, the support material, and the crosslinking material, suspending the enzyme in an aqueous medium, and combining the other materials provided to form a flocculent that can be isolated by standard methods. In some instances, the support material should be added before the crosslinking material, whereas in other instances, the crosslinking material should be added before the support material depending on process effectiveness and activity considerations. The aqueous flocculent can be used directly or isolated, dried, and formulated into particles having a desirable size and shape, depending on the intended application. The activity of certain immobilized enzymes was significantly and surprisingly increased upon heating the solid at an elevated temperature.

The following defined terms are utilized in the present disclosure and carrying with them the meanings specifically described herein.

Support Matrix: One or more materials used to form a particle to impart mechanical and enzymatic stability upon an enzyme that can include within it, crosslinkers, reactive polymers, support materials, and biomass.

Biomass: Material produced by a biological source such as microorganisms, plants, and/or other living organisms such as mollusks, insects, or crustaceans, or portions of organisms such exoskeletons and/or shells (both organic and mineral-based). Such materials may be mechanically processed (grinding, pulverizing, and the like), but not chemically treated or processed.

Support Material: Materials used individually or in combination in a Support Matrix, such as Biomass, synthetically manufactured polymers, and/or other non-organic materials.

Crosslinking Agent: chemical reagents containing two or more reactive ends that are used to covalently bond specific functional groups on enzymes and support materials, for instance, attaching amine groups with aldehydes.

Reactive Polymers: includes polymers with reactive pendant groups which can react with the crosslinkers.

Immobilization Procedures

The following examples are intended to be illustrative of the present disclosure and are not intended to otherwise limit the disclosure in any manner. As demonstrated by the examples that follow, enzymes from a wide range of enzyme classes that include Oxidoreductases, Transferases, Hydrolases, Lyases, Isomerases, and Ligases can be utilized according to this present disclosure. The ODE enzymes used in the following examples were immobilized using host cells as either a cell slurry or lysed cell material. In some examples, purified enzymes were used. Support materials may also include synthetic and/or polymeric materials such as polyethylenimine, chitosan, polypyrrole, or other suitable material. Optionally, the support material may comprise a combination of one or more biosupport materials and/or polymeric support materials. Cross linking comprised polyfunctional materials such as glutaraldehyde (GA), disuccinimidyl suberate (DSS), dimethyl pimelimidate (DMP), dimethyl adipimidate (DMA), cyanuric chloride (CyC), succinic acid (SA), hexamethylene diisocyanate (HDI), and/or other reagents capable of crosslinking to amines.

An enzyme is provided (isolated or contained in myceliuma mixture which may contain other proteins or a cell slurry) and suspended in an aqueous buffer solution. A support is added with stirring which is continued for about 1 hour until the solution is well mixed. Optionally, a volume of additional deionized water may be added as desired. A crosslinker is added with continued agitation to cause the immobilized enzyme to flocculate. The solid can be isolated and dried utilizing standard procedures. This is but one example of a general immobilization procedure. In other examples, the components may be added in a different order, two or more may be added simultaneously, and/or the steps may be performed over a longer or shorter period of time. The following examples are provided for illustrative purposes, and are not intended to limit the disclosed technology in any manner.

Immobilization Process for Organophosphate Hydrolase

In the following examples, the OPH enzyme used is of the variety disclosed in U.S. patent application Ser. No. 12/241,574 ('574 application) titled Differentially Fluorescent Yeast Biosensors for the Detection and Biodegradation of Chemical Agents, which was filed on Sep. 30, 2008. The methods and techniques described herein may also be applied to other varieties of OPH and/or to varieties of OPH produced using methods other than those disclosed in the '574 application. The methods and techniques described herein may also be applied to enzymes other than OPH. Organophosphate-degrading enzymes such as other aryldialkylphosphatases (E.C. 3.1.8.1) and diisopropyl-fluorophosphatases (E.C. 3.1.8.2) and the like may also be used. In some examples, an organophosphate-degrading enzyme is one which acts on one or more bonds connecting a phosphorous atom with a molecule, although the disclosed techniques may also be applied to enzymes which degrade or break down organophosphates using different mechanisms. Optionally, the techniques and methods disclosed herein may also be adapted and applied to combinations of two or more enzymes. In other examples the methods and techniques disclosed herein may be adapted and applied to two or more enzymes individually and then the resulting immobilized enzymes may be combined as desired for a particular application.

In one example, the enzyme is immobilized using biomass which was previously used to produce the enzyme. In this particular example, the enzyme is produced by a fermentation which generates a fermentation broth containing the enzyme and the biomass of the organisms which created the enzyme. The broth is removed from the fermenter and the solid material is dried and optionally processed to yield particles of a desired size. Optionally, small molecules may be removed from the solution prior to drying. Additionally, enzyme cofactors, substances that form a solid material containing the biomass and enzyme, or additional substances may be added to the fermenter prior to removal of the fermentation broth, and/or directly to the solid material either before or after drying as desired.

The immobilized enzyme formed by such a process is may be less expensive than other immobilization processes because there is no cost for a solid matrix material used to support the enzyme. Also, less enzyme and enzyme activity is lost when the enzyme is retained with the biomass.

This immobilized enzyme may demonstrate greater thermal stability than the free enzyme. Hence it can withstand greater temperature fluctuations in both storage and usage and still maintain activity. The immobilized enzyme may also demonstrate greater activity in solvent solutions. Increased activity in solvents other than water is beneficial because some organophosphorus compounds are more soluble in solvents other than water. Solvents that might be considered are alcohol/water mixtures such as 20 percent methanol in water as well as other solvents.

Another aspect of the present disclosure is to provide an inexpensive immobilized enzyme which exhibits increased biodegradation under a variety of environmental conditions. In some examples, most or all of the chemical components which comprise an immobilized enzyme will exhibit increased biodegradation in a biodegradable immobilized enzyme product. In one example, an enzyme is immobilized using the biomass which was used to produce the enzyme where the biomass itself is biodegradable. In other examples, biomass from other fermentations could be used to immobilize a soluble enzyme first produced using other methods. In still other examples, the biomass material used is insoluble or has limited solubility in water.

The following examples describe methods for immobilizing enzymes using the enzyme OPH. The use of one specific enzyme (OPH) in the examples was done for the sake of convenience. The disclosed methods and techniques for immobilizing enzymes are not limited to OPH. It is understood that one of ordinary skill in the art would be able to adapt the disclosed methods and techniques to immobilize a wide variety of other enzymes including, but not limited to, lactase, glucose isomerase, catalase, invertase, phytase, amyloglucosidase, glucose oxidase, penicillin acylase, and the like.

Immobilization of Enzyme-Containing Cells

Cell Growth, Enzyme Production, Initial Preparation

In one example, production of OPH from engineered *E. coli* begins with the preparation of a culture stock solution. The initial solution, 125 mL, consisting of 25 g/L LB Broth, is sterilized at 121° C. for 15 minutes. After sterilization it is allowed to cool and 50 µg/mL of kanamycin and 50 µg/mL of chloramphenicol are aseptically added to the stock solution. A seed culture is prepared from 2 mL of this stock solution and 1 colony of *E. coli* harvested from an agar plate that was previously streaked or inoculated with the desired *E. coli* organism. This 2 mL solution is incubated for 24 hours at 37° C. on a shake table at 150 RPM. After the incubation period has ended, seed culture solution is added in a sterile manner at 1% v/v to a larger volume (20 mL) of the culture stock solution, identified as the starter culture. This starter culture is then incubated for 24 hours at 37° C. on a shake table at 150 RPM.

The fermentation broth solution, consisting of 15 g/L dextrose, 10 g/L yeast extract, and 5 µg/L Pharmamedia in tap water is introduced into the 14 liter fermentation vessel (10 liter working volume) New Brunswick BioFlo 3000 fermenter. This solution is sterilized in the fermentation vessel at 121° C. for 15 minutes. After sterilization the vessel is cooled and 50 µg/mL of kanamycin and 50 µg/mL chloramphenicol are aseptically added to the fermentation broth. The fermentation control points are set at 37° C., pH 7.0, 35% dissolved oxygen, 8 SLPM of filtered dry air, and 100-600 rpm agitation. The agitation rate was used to control the dissolved oxygen and the temperature was controlled by varying the rate of cooling water to the fermenter. The vessel was allowed to equilibrate in temperature, dissolved oxygen, pH and other chemical characteristics. The fermentation vessel was then inoculated with 1% v/v of the starter culture. The OD 600 of the fermentation broth was regularly monitored by taking a sample from the fermentation vessel while maintaining the sterility of the vessel. A Pharmacia Ultrospec III spectrophotometer was used to measure light transmission at 600 nm. When the OD 600 surpasses a value of 3.5 the *E. coli* was induced to produce OPH through the sterile addition of 47.7 mg/L IPTG and 13.0 mg/L $CoCl_2$. The induced fermentation was allowed to proceed for 4 hours at which point the broth was harvested. The harvested volume from the fermenter was approximately 7.75 liters.

The harvested broth was concentrated 5-fold through microfiltration and diafiltration with PBS through a 0.14 µm ceramic microfilter. The diafiltration through the microfilter removed soluble salts and polymers from the solution. The enzyme is contained in the *E. coli* cells and hence is retained by the microfilter. The filter permeate was analyzed to determine that little enzyme is lost in this filtration. The final volume of concentrated microfiltered cells was approximately 1.5 liters. The concentrated broth was then centrifuged in aliquots of approximately 50 mL at 3000×G for 30 minutes and the supernatant was removed. The cell pellets from this process were stored at −20° C. until needed.

Example 1

Cell Immobilization Procedure Using PEI and Glutaraldehyde

For immobilization processes one or more of the frozen pellets was removed from the freezer and allowed to thaw. 10 g of the thawed cell pellet was resuspended in 100 mL of pH 7.0 phosphate buffer solution (PBS). Glutaraldehyde (GA) was added slowly to this volume over a period of 1 minute to a final concentration of 0.2% (v/v) and mixed for one hour at room temperature. The solution was then diluted with two volumes of deionized water to a total volume of approximately 300 ml and varying amounts up to 0.075% (v/v) polyethylenimine (PEI) was slowly dripped into the solution to flocculate the cells. Immobilized cell mass was collected by centrifugation at 750×G for 10 minutes yielding approximately 10 grams of wet immobilized cells. The resulting solids were spread out and dried at room temperature for 24 hours. The dried material was then collected and mechanically ground to the desired particle size using a mortar and pestle or wet milling by glass beads in a test tube. If necessary these particles were again dried.

Different variations of this process are possible including the order of addition of PEI and GA, the sequential addition of PEI and GA intermittently, the time between additions, the simultaneous addition of PEI and GA, the amounts and concentrations of PEI and GA added, etc. In the first variation in the process, the order of addition of PEI and GA was inverted, although the same total concentration of these materials was maintained. Otherwise the immobilization was performed using the same procedures. A second immobilization variation from the original involved using twice as much GA which was added in the same time and reacted for the one hour as before. The third variation from the original immobilization procedure used one-half of the original amount of PEI. In yet another variation, GA could be replaced with any suitable di-aldehyde.

Example 2

Biodegradable Immobilized Enzymes

The immobilizations discussed above involved whole cells, PEI, and glutaraldehyde. The whole cells and the glutaraldehyde are biodegradable but the PEI is not. In some applications, it would be desirable to have the entire immobilized particle to be biodegradable. Therefore, PEI could be replaced with another, more biodegradable material. Materials suitable could include biodegradable polymers with chemical groups that can react with glutaraldehyde such as proteins, gelatins, wool, chitins, chitosan, and the like.

For the formation of a biodegradable whole cell immobilized enzyme, the immobilization process above was carried out with chitosan (CHI) substituted for the PEI. For immobilization processes one or more of the frozen pellets was removed from the freezer and allowed to thaw. 10 g of the thawed cell pellet was resuspended in 100 mL of pH 7.0 PBS. GA was added slowly to this volume over a period of 1 minute to a final concentration of 0.2% (v/v) and mixed for one hour at room temperature. The solution was then diluted with two volumes of deionized water to a total volume of approximately 300 ml and varying amounts up to 1 g of CHI was slowly added to the solution to flocculate the cells. Immobilized cell mass was collected by centrifugation at 750×G for 10 minutes yielding approximately 10 grams of wet immobilized cells. The resulting solids were spread out and dried at room temperature for 24 hours. The dried material was then collected and mechanically ground to the desired particle size using a mortar and pestle or wet milling by glass beads in a test tube. If necessary these particles were again dried.

Example 3

Immobilization of Soluble OPH Enzyme

Sometimes an enzyme is available in a soluble form (e.g. the enzyme is excreted by the microorganism producing the enzyme). A biodegradable immobilized enzyme may be a desirable product using such a soluble enzyme. One advantage of whole cell immobilization is the inexpensive biodegradable biomass from the organism which produced the enzyme. It is also possible for example to form an immobilized enzyme by using the soluble enzyme, biomass from another fermentation (often waste), chitosan, and glutaraldehyde to form an inexpensive biodegradable immobilized enzyme.

Initial Preparation of Soluble OPH Enzyme

Soluble OPH enzyme was harvested from the frozen cell pellets through chemical lysis and chromatography process. Frozen cell pellets were thawed for 5 minutes in a room temperature water bath. Cells were initially lysed with 5 mL lysis buffer (98.8% YPER, 1% protease inhibitor, 0.2% DNAse I) per gram of cell pellet. The pellet was loosened with a Teflon coated spatula and an additional 3-5 mL of lysis buffer was used to rinse cell material off the spatula into the rest of the lysate. The lysate was then incubated on ice on an orbital shaker for 40 minutes. Following the incubation the lysate was clarified through centrifugation for 20 minutes at 20,000×G and 4° C. The supernatant from the centrifugation was collected and stored at 4° C. until needed.

For the chromatography process, the 8 mL of lysate was added per 2 mL of prepared NTA-Nickel resin in a centrifuge tube. The lysate/resin mixture was incubated on an orbital shaker for 30 minutes at 4° C. Following incubation the mixture was centrifuged at 800×G for 5 minutes and the supernatant removed. 13 mL binding buffer (50 mM phosphate buffer, 500 mM NaCl) per 2 mL resin was added to the column. The resin was gently resuspended and allowed to settle before centrifugation at 800×G for 5 min. Again the supernatant was removed and 13 mL of wash buffer (30 mM imidazole, 50 mM phosphate buffer, 500 mM NaCl) per 2 mL resin was added. After resuspending the resin and allowing it to settle it was centrifuged at 800×G for 5 min, and the supernatant was removed. The process with the wash buffer was repeated one time. Following the wash step, 3 mL of elution buffer (250 mM imidazole, 50 mM phosphate buffer, 500 mM NaCl) was added per 2 mL of resin. This final mixture was incubated on an orbital shaker at room temperature for 10 minutes. After allowing the resin to settle it was centrifuged at 800×G for 5 min, the supernatant (elution fraction) was collected and held at 4° C. until needed.

Soluble enzyme was concentrated in the elution fraction by centrifugal filtration employing 10,000 kDa filters. This process also served to exchange the buffer solution containing the protein. 12 mL of elution fraction was added to each filtration device and centrifuged at 5000×G concentrating the material to 1 mL 10 minutes). Permeate was removed and the filtrate was diluted back to 12 mL with storage buffer (50 mM phosphate, 500 mM NaCl). This process was repeated two times upon which the filtrate was collected and stored at 4° C. until needed.

Immobilization Procedures Using Soluble OPH

For immobilization of the soluble enzyme, 0.5 mL of concentrated OPH filtrate was diluted to 1.5 mL with DI water. 6 mg of chitosan was added to this solution and allowed to mix for 30 minutes. The solution was then further diluted to 5 mL with DI water and up to 12 µA of a 25% GA solution was slowly dripped into this solution. After the reaction with GA, the material was allowed to gravimetrically settle for several hours and ~4 mL of the supernatant was carefully removed such that the immobilized solids were left undisturbed. This material was stored at 4° C. until needed. A variant on this immobilization process involved the addition of 165 mg of sterilized *A. niger* mycelium (~12% solids) following the addition of chitosan.

Example 4

Variations on Immobilization of OPH Contained in Cells

Slurry containing OPH and related cells in 100 mL of PBS (pH 7.5) was prepared. Glutaraldehyde was added and the slurry stirred for 1 hour at room temperature. Deionized water (200 mL) was added, followed by the addition of chitosan. Flocculation initiated and continued while stirring was continued for several minutes. When flocculation was complete, the solid was isolated and dried using one of two processes. The first process isolated the material by transferring it to centrifuge tubes, and centrifuging at 750-1000×G for about 10 minutes. Drying of the particulate mass was performed by air drying for 24 hours. When desired, pellets were formed from the moist solid before drying. The alternate process took the flocculated product and transferred it to lyophilization tubes and lyophilized using standard techniques until a dry product was obtained. Through either process powdered material was obtained by mechanically grinding the dried material to the desired size.

Several immobilized OPH enzymes were prepared utilizing glutaraldehyde as the crosslinker, with supports including polyethylenimine, chitosan, polypyrrole, and a biomass which includes dry cells containing OPH. Each procedure began by suspending a quantity of OPH enzyme in a starting buffer of phosphate buffered saline and the procedure was allowed to continue long enough for substantially complete flocculation of the final immobilized enzyme. Chart 1 below provides information related to the preparation of these immobilized variations. Differences in the procedures used in each example are noted in the chart below.

CHART 1

| | | | materials | | Starting Buffer | | | Diluent Buffer | | | Procedure | |
|---|---|---|---|---|---|---|---|---|---|---|---|---|
| ID | Enzyme (mg) | Cross-linker (g) | Bio-Mass (g) | Reactive Ploymer (g) | ID | pH | Vol. (mL) | ID | pH | Vol. (mL) | T (° C.) | Notes |
| OPH-6 | OPH - 6.19 | GA - 0.20 | EC - 6.04 | PEI - 0.23 | PBS | 7.0 | 50 | DI H$_2$O | 7.0 | 100 | 25 | a, b, d, h |
| OPH-5 | OPH - 5.97 | GA - 0.20 | EC - 3.24 | PEI - 0.23 | PBS | 7.0 | 50 | DI H$_2$O | 7.0 | 100 | 25 | a, c, d, i |
| OPH-8 | OPH - 5.83 | GA - 0.20 | EC - 3.16 | PEI - 0.11 | PBS | 7.0 | 50 | DI H$_2$O | 7.0 | 100 | 25 | a, b, d, h |
| OPH-4 | OPH - 11.13 | GA - 0.40 | EC - 6.04 | CHI - 0.23 | PBS | 7.0 | 50 | DI H$_2$O | 7.0 | 100 | 25 | a, b, d, h |
| OPH-7 | OPH - 4.14 | GA - 0.20 | EC - 2.25 | CHI - 0.23 | PBS | 7.0 | 50 | DI H$_2$O | 7.0 | 100 | 25 | a, b, d, j |
| OPH-10A | OPH - 1.35 | GA - 0.05 | EC - 0.73 | CHI - 0.06 | PBS | 7.0 | 47 | DI H$_2$O | 7.0 | 94 | 25 | a, b, d, j |
| OPH-11A | OPH - 0.28 | GA - 0.11 | EC - 0.15 | CHI - 0.12 | PBS | 7.0 | 50 | DI H$_2$O | 7.0 | 100 | 25 | a, b, d, j |
| OPH-16A | OPH - 1.30 | GA - 0.05 | EC - 0.71 | CHI - 0.11 | PBS | 7.0 | 47 | DI H$_2$O | 7.0 | 94 | 25 | a, b, d, j |
| OPH-16B | OPH - 1.26 | GA - 0.10 | EC - 0.69 | CHI - 0.23 | PBS | 7.0 | 50 | DI H$_2$O | 7.0 | 100 | 25 | a, b, d, j |
| OPH-15 | OPH - 4.00 | GA - 0.20 | EC - 2.17 | CHI - 0.69 | PBS | 7.0 | 50 | DI H$_2$O | 7.0 | 100 | 25 | a, b, d, j |
| OPH-10B | OPH - 1.24 | GA - 0.10 | EC - 0.68 | CHI - 0.10 PPY - 0.01 | PBS | 7.0 | 47 | DI H$_2$O | 7.0 | 94 | 25 | a, b, d, k |
| OPH-11B | OPH - 1.52 | GA - 0.15 | EC - 0.83 | CHI - 0.08 PPY - 0.08 | PBS | 7.0 | 69 | DI H$_2$O | 7.0 | 138 | 25 | a, b, d, k |
| OPH-14 | OPH - 2.52 | GA - 0.20 | EC - 1.37 | PPY - 0.23 | PBS | 7.0 | 50 | DI H$_2$O | 7.0 | 100 | 25 | a, b, d, l |
| OPH-3A | OPH - 0.84 | GA - 0.07 | EC - 0.46 | YE - 0.15 | PBS | 7.0 | 32 | DI H$_2$O | 7.0 | 64 | 25 | a, b, d, m |
| OPH-3B | OPH - 0.93 | GA - 0.07 | EC - 0.51 | PM - 0.15 | PBS | 7.0 | 32 | DI H$_2$O | 7.0 | 64 | 25 | a, b, d, n |
| OPH-3C | OPH - 0.76 | GA - 0.07 | EC - 0.41 AN - 0.11 | | PBS | 7.0 | 32 | DI H$_2$O | 7.0 | 64 | 25 | a, b, e, o |
| OPH-12A | OPH - 0.77 | GA - 0.07 | EC - 0.42 | CHI - 0.08 | PBS | 7.0 | 32 | DI H$_2$O | 7.0 | 64 | 40 | a, b, f, o |
| OPH-9B | OPH - 0.58 | GA - 0.12 | EC - 0.32 | CHI - 0.08 | PBS | 7.0 | 32 | HEPES | 8.0 | 64 | 5 | a, g, o, i |
| OPH-12B | OPH - 0.79 | GA - 0.07 | EC - 0.43 | CHI - 0.08 | PBS | 4.0 | 32 | DI H$_2$O | 4.0 | 64 | 25 | a, g, o, i |
| OPH-12C | OPH - 0.72 | GA - 0.07 | EC - 0.39 | CHI - 0.15 | PBS | 10.0 | 32 | DI H$_2$O | 10.0 | 64 | 25 | a, g, o, i |
| OPH-9A | OPH - 0.70 | DMP - 0.09 | EC - 0.38 | CHI - 0.08 | PBS | 7.0 | 32 | HEPES | 8.0 | 64 | 25 | a, g, o, p |
| OPH-9C | OPH - 0.53 | DSS - 0.09 | EC - 0.29 | CHI - 0.08 | PBS | 7.0 | 32 | HEPES | 8.0 | 64 | 40 | a, g, o, q |
| OPH-1A | OPH - 0.78 | SA - 0.10 | EC - 0.42 | CHI - 0.08 | PBS | 7.0 | 32 | HEPES | 8.0 | 64 | 5 | a, g, o, r |

CHART 1-continued

| | materials | | | | Starting Buffer | | | Diluent Buffer | | | Procedure | |
|---|---|---|---|---|---|---|---|---|---|---|---|---|
| ID | Enzyme (mg) | Cross-linker (g) | Bio-Mass (g) | Reactive Polymer (g) | ID | pH | Vol. (mL) | ID | pH | Vol. (mL) | T (° C.) | Notes |
| OPH-1B | OPH - 212 | CC - 0.17 | EC - 1.15 | CHI - 0.08 | PBS | 7.0. | 32 | HEPES | 8.0 | 64 | 25 | a, g, o, s |
| OPH-1C | OPH - 0.96 | DCH - 0.11 | EC - 0.52 | CHI - 0.08 | PBS | 7.0 | 32 | HEPES | 8.0 | 64 | 25 | a, g, o, t |

Abbreviations
OPH—organophosphorus hydrolase
GA—glutaraldehyde
EC—*E. coli* cells
CHI—chitosan
PPY—polypyrrole
YE—yeast extract
PM—pharmamedia
AN—*A. niger* mycelium
DMP—dimethyl pimelimidate
DSS—disuccinimidyl suberate
SA—succinic acid
CC—cyanuric chloride
DCH—1,6 diisocyantohexane Procedural Notes
a - suspend OPH and biosupport in starting buffer
b - add GA and mix for about 1 hour
c - add PEI and mix for about 1 hour
d - add diluent to buffer solution
e - add AN to diluent buffer and stir for about 30 minutes
f - add CHI to diluent buffer and stir for about 30 minutes
g - add CHI to diluent buffer
h - slowly add PEI
i - slowly add GA
j - slowly add CHI
k - slowly add CHI and PPY
l - slowly add PPY
m - slowly add YE
n - slowly add PM
o - slowly add diluent solution
p - slowly add DMP
q - slowly add DSS
r - slowly add SA
s - slowly add CC
t - slowly add DCH

Example 5

Immobilization of Soluble Xylanase Enzyme

A slurry containing xylanase in 100 mL of PBS (pH 7.5) was prepared. *Aspergillus niger* and chitosan were added and the suspension stirred for 1 hour at room temperature. Deionized water (200 mL) was added followed by the addition of glutaraldehyde. Flocculation initiated and continued while stirring was continued for several minutes. When flocculation was complete, the solid was isolated and dried. Powdered material was obtained by mechanically grinding the dried material to the desired size.

Unless otherwise noted, all of the examples listed in Chart 1 were conducted at a temperature of 25° C. Each procedure began by suspending a quantity of xylanase enzyme in a starting buffer of deionized water and the procedure was allowed to continue long enough for substantially complete flocculation of the final immobilized enzyme. Differences in the procedures used in each example are noted in the chart below. Some immobilization tests were performed without biomass in order to simplify investigations of immobilization reaction conditions.

CHART 2

| ID | Materials | | | | Starting Buffer | | Diluent Buffer | | | Procedure Notes |
|---|---|---|---|---|---|---|---|---|---|---|
| | Enzyme (mg) | Crosslinker (g) | Bio-Mass (g) | Reactive Polymer (g) | pH | Vol. (mL) | ID | pH | Vol. (mL) | |
| XY-1 | XY - 100 | GA - 0.70 | | CHI - 1.20 | 7.0 | 50 | DI | 7.0 | 100 | a, b, c |
| XY-2 | XY - 100 | GA - 0.70 | AN - 10.00 | | 7.0 | 50 | DI | 7.0 | 100 | a, d, c |
| XY-3 | XY - 100 | GA - 0.70 | | CHI - 1.20 | 7.0 | 150 | | | | f, e |
| XY-4 | XY - 100 | GA - 0.66 | | CHI - 1.32 | 4.0 | 150 | | | | f, e |
| XY-5 | XY - 100 | GA - 0.66 | | CHI - 1.32 | 10.0 | 150 | | | | f, e |

Abbreviations
XY—xylanase
GA—glutaraldehyde
AN—*A. niger* mycelium
CHI—chitosan
DI—deionized water Procedural Notes
a - add GA and let mix for about 1 hour
b - suspend CHI in diluent buffer
c - slowly add diluent solution to starting solution
d - suspend AN in diluent buffer
e - slowly add GA to solution
f - suspend CHI in starting buffer Example 6

Immobilization of Soluble Peroxidase Enzyme

A slurry containing peroxidase in 100 mL of PBS (pH 7.5) was prepared. Chitosan was added and the suspension stirred for 15 minutes at room temperature. Deionized water (50 mL) was added followed by the addition of glutaraldehyde. Flocculation initiated and continued while stirring was continued for several minutes. When flocculation was complete, the solid was isolated and dried using standard methods. Powdered material was obtained by mechanically grinding the dried material to the desired size.

Unless otherwise noted, all of the examples listed in Chart 4 were conducted at a temperature of 25° C. Each procedure began by suspending a quantity of peroxidase enzyme derived from horseradish in a starting buffer solution as noted in the chart, and the procedure was allowed to continue long enough for substantially complete flocculation of the final immobilized enzyme. Differences in the procedures used in each example are noted in the chart below. Several immobilizations were performed without biomass material in the composition to explore the direct effectiveness of crosslinker materials on the enzyme.

CHART 3

| ID | Materials | | | | Starting Buffer | | | Procedure Notes |
|---|---|---|---|---|---|---|---|---|
| | Enzyme (mg) | Crosslinker (g) | Bio-Mass (g) | Reactive Polymer (g) | ID | pH | Vol. (mL) | |
| PO-1 | PO - 9.9 | GA - 0.66 | | CHI - 1.32 | PBS | 7.0 | 150 | a, d |
| PO-2 | PO - 9.9 | GA - 0.66 | AN - 0.66 | CHI - 0.66 | PBS | 7.0 | 150 | b, d |
| PO-3 | PO - 5.2 | GA - 0.66 | | PPY - 0.26 | PBS | 7.0 | 150 | c, d |
| PO-4 | PO - 9.9 | GA - 0.40 | | CHI - 1.88 | PBS | 7.0 | 150 | a, d |
| PO-5 | PO - 10.1 | DMP - 0.09 | | CHI - 1.81 | HEPES | 8.0 | 150 | a, e |
| PO-6 | PO - 8.4 | DSS - 0.09 | | CHI - 1.81 | HEPES | 8.0 | 150 | a, f |
| PO-7 | PO - 9.9 | GA - 0.19 | | CHI - 1.81 | HEPES | 8.0 | 150 | a, d |
| PO-8 | PO - 8.0 | SA - 0.1 | | CHI - 1.82 | HEPES | 8.0 | 150 | a, g |

CHART 3-continued

| | Materials | | | Reactive | Starting Buffer | | | |
|---|---|---|---|---|---|---|---|---|
| ID | Enzyme (mg) | Crosslinker (g) | Bio-Mass (g) | Polymer (g) | ID | pH | Vol. (mL) | Procedure Notes |
| PO-9 | PO - 9.0 | CC - 0.17 | | CHI - 1.83 | HEPES | 8.0 | 150 | a, h |
| PO-10 | PO - 9.7 | DHC - 0.11 | | CHI - 1.80 | HEPES | 8.0 | 150 | a, i |

Abbreviations
PO—peroxidase (from horseradish)
GA—glutaraldehyde
DSS—disuccinimidyl suberate
SA succinic acid
CC—cyanuric chloride
PPY—polypyrrole
DCH—1,6 diisocyantohexane
AN—*A. niger* mycelium
CHI—chitosan
DMP—dimethyl pimelimidate
Procedural Notes
a - mix PO and CHI in starting buffer
b - mix PO, AN, and CHI in starting buffer
c - mix PO and PPY in starting buffer
d - slowly add GA to solution
e - slowly add DMP to solution
f - slowly add DSS to solution
g - slowly add SA to solution
h - slowly add CC to solution
i - slowly add DCH to solution Example 7

Immobilization of Soluble Alcohol Dehydrogenase Enzyme

A slurry containing alcohol dehydrogenase in 150 mL of PBS (pH 7.5) was prepared. Chitosan was added and the suspension stirred for 15 minutes at room temperature. This was followed by the addition of glutaraldehyde. Flocculation initiated and continued while stirring was continued for several minutes. When flocculation was complete, the solid was isolated and dried.

Unless otherwise noted, all of the examples listed in Chart 2 were conducted at a temperature of 25° C. Each procedure began by suspending a quantity of alcohol dehydrogenase enzyme in a starting buffer of phosphate buffered saline (pH=7.0) and the procedure was allowed to continue long enough for substantially complete flocculation of the final immobilized enzyme. In each example below where a diluent was used, the diluent comprised 100 mL of deionized water having a pH of 7.0. Differences in the procedures used in each example are noted in the chart below.

CHART 4

| | Materials | | | | Starting | |
|---|---|---|---|---|---|---|
| ID | Enzyme (mg) | Crosslinker (g) | Bio-Mass (g) | Reactive Polymer (g) | Buffer Vol. (mL) | Procedure |
| AD-1 | AD - 20.0 | GA - 0.66 | | CHI - 1.32 | 50 | Suspend AD in Starting Buffer<br>Add GA and let mix for 15 min<br>Add Diluent Buffer to Starting solution<br>Slowly add CHI<br>Allow for completion of flocculation |
| AD-2 | AD - 20.0 | GA - 0.66 | AN - 0.66 | CHI - 0.66 | 50 | Suspend AD in Starting Buffer<br>Add ½ Diluent Buffer to Starting solution.<br>Slowly add GA, and stir for 30 min<br>Add AN and CHI to remaining half of Diluent Buffer.<br>Slowly mix Solutions<br>Allow for completion of flocculation |
| AD-3 | AD - 17.5 | GA - 0.66 | EC - 0.46 | CHI - 1.01 | 50 | Suspend AD and EC in Starting Buffer<br>Add CHI and let mix for about 15 min<br>Add Diluent Buffer to Starting solution<br>Slowly add GA<br>Allow for completion of flocculation |

CHART 4-continued

| ID | Enzyme (mg) | Crosslinker (g) | Bio-Mass (g) | Reactive Polymer (g) | Starting Buffer Vol. (mL) | Procedure |
|---|---|---|---|---|---|---|
| AD-4 | AD - 19.9 | GA - 0.66 | EC - 0.38 | CHI - 1.00 | 50 | Suspend AD and EC in Starting Buffer<br>Add CHI and let mix for about 15 min<br>Add Diluent Buffer to Starting soln.<br>Slowly add GA<br>Allow for completion of flocculation |
| AD-5 | AD - 31.4 | GA - 0.10 | | CHI - 1.87 | 150 | Suspend AD and CHI in Starting Buffer<br>Stir till well mixed<br>Slowly add GA<br>Allow for completion of flocculation |

Abbreviations
AD—alcohol dehydrogenase
GA—glutaraldehyde
AN—*A. niger* mycelium
CHI—chitosan
EC—*E. coli* cells Example 8

Immobilization of Soluble Pyruvate Decarboxylase Enzyme

A slurry containing alcohol pyruvate decarboxylase in 150 mL of HEPES (pH 7.5) was prepared. Chitosan was added and the suspension stirred for several minutes at room temperature. This was followed by the addition of glutaraldehyde. Flocculation initiated and continued while stirring was continued for several minutes. When flocculation was complete, the solid was isolated and dried.

Unless otherwise noted, all of the examples listed in Chart 3 were conducted at a temperature of 25° C. Each procedure began by suspending a quantity of pyruvate decarboxylase enzyme in a starting buffer of phosphate buffered saline (pH=7.0) and the procedure was allowed to continue long enough for substantially complete flocculation of the final immobilized enzyme. Differences in the procedures used in each example are noted in the chart below.

CHART 5

| ID | Enzyme (mg) | Crosslinker (g) | Bio-Mass (g) | Reactive Polymer (g) | Starting Buffer Vol. (mL) | Procedure Preparation Method |
|---|---|---|---|---|---|---|
| PDC-1 | PDC - 8.2 | GA - 0.66 | | CHI - 1.32 | 150 | Suspend PDC and CHI in Starting Buffer<br>Stir till well mixed<br>Slowly add GA<br>Allow for completion of flocculation |
| PDC-2 | PDC - 8.1 | GA - 0.66 | AN - 0.66 | CHI - 0.66 | 150 | Suspend PDC, AN, and CHI in Starting Buffer<br>Stir till well mixed<br>Slowly add GA<br>Allow for completion of flocculation |
| PDC-3 | PDC - 9.9 | GA - 0.66 | EC - 0.46 | CHI - 1.00 | 150 | Suspend PDC, EC, and CHI in Starting Buffer<br>Stir till well mixed<br>Slowly add GA<br>Allow for completion of flocculation |
| PDC-4 | PDC - 10.7 | GA - 0.66 | EC - 0.38 | CHI - 1.00 | 150 | Suspend PDC, EC, and CHI in Starting Buffer<br>Stir till well mixed<br>Slowly add GA<br>Allow for completion of flocculation |
| PDC-5 | PDC - 10.6 | GA - 0.16 | AN - 0.63 | CHI - 0.67 | 150 | Wash AN in PBS<br>Suspend PDC, AN, and CHI in Starting Buffer<br>Stir till well mixed<br>Slowly add GA<br>Allow for completion of flocculation |

CHART 5-continued

| | Materials | | | | Starting | |
|---|---|---|---|---|---|---|
| ID | Enzyme (mg) | Crosslinker (g) | Bio-Mass (g) | Reactive Polymer (g) | Buffer Vol. (mL) | Procedure Preparation Method |
| PDC-6 | PDC - 10.9 | GA - 0.16 | AN - 0.65 | CHI - 0.68 | 50 | Suspend PDC and CHI in Starting Buffer<br>Stir till well mixed<br>Slowly add GA<br>Mix for about 1 hour<br>Add 100 mL AN suspension<br>Allow for completion of flocculation |

Abbreviations
PDC—pyruvate decarboxylase
GA—glutaraldehyde
AN—*A. niger* mycelium
CHI—chitosan
EC—*E. coli* cells Enzyme Activity Testing One advantage of the immobilization is to increase the stability of the enzyme for temperature, solvent activity, and other improvements in the characteristics of the enzyme. To determine the improvements it is necessary to measure the activity of the enzyme.

Organophosphate Hydrolase

OPH hydrolyzes'many different organic compounds which contain orthophosphate moieties such as the following list of compounds: acephate, coumaphos, demeton, diazinon, dursban, malathion, paraoxon, parathion, methyl paraoxon, and methyl parathion. The general reaction scheme is outlined as follows:

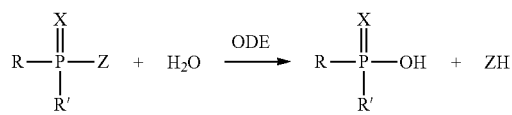

where X is either oxygen or sulfur, R and R' are alkyl groups, and Z is either an aryloxy group, a fluorine group, a thiol group, or a cyanide. It is understood that other methods may also be used to test enzymatic activity, including examining an immobilized enzyme's ability to hydrolyze organic compounds other than those listed.

The activity of the enzyme defined as the number of phosphate bonds broken per unit time depends greatly on the substrate. Paraoxon was used as the substrate of choice for the enzyme activity measurement in this test, although other substrates may also be used. The reaction has the following stoichiometry.

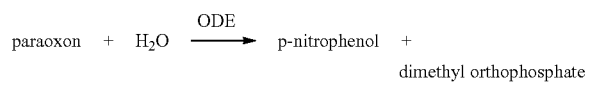

The p-nitrophenol adsorbs light at 410 nm and hence the formation of this compound can be measured as a function of time. From this measurement it is possible to calculate the kinetics for the reaction. The rate is calculated from the linear section of the graph of absorbance due to p-nitrophenol vs. time. The selection of the linear section can vary somewhat adding uncertainty to the estimate of the reaction rate.

Experimentally, an immobilized enzyme sample (10 milligrams) was added to a substrate solution (12 mL) at a pH of 7.5 at room temperature and stirred. Standard assay solutions consisted of 50 mM HEPES buffer, 0.1 mM $CoCl_2$, and 0.1 mM paraoxon in deionized water. The initial velocity of the enzyme is determined by sampling the assay solution and measuring the concentration of the assay product versus time. Thus the concentration of p-nitrophenol was determined through spectrophotometer measurements at 410 nm every 3 minutes. The enzyme's activity was determined by the decomposition of paraoxon (reported as (units/mg organophosphorus hydrolase enzyme)). One unit results in the decomposition of 1.0 μmole of paraoxon per minute at pH 7.5 at 25° C. Immobilized enzymes had a particle size of about 200 μm. Table 5 provides the OPH enzyme's activity. Other commonly accepted methods for determining enzyme activity could also be used.

TABLE 1

| | Activity [units/g OPH] |
|---|---|
| OPH-1A | 17.9 |
| OPH-1B | 0.3 |
| OPH-1C | 11.1 |
| OPH-3A | 7.1 |
| OPH-3B | 8.2 |
| OPH-3C | 7.4 |
| OPH-4 | 1.8 |
| OPH-5 | 1.5 |
| OPH-6 | 0.7 |
| OPH-7 | 2.7 |
| OPH-8 | 1.2 |
| OPH-9A | 27.1 |
| OPH-9B | 59.9 |
| OPH-9C | 4.82 |
| OPH-10A | 5.1 |
| OPH-10B | 5.7 |
| OPH-11A | 6.0 |
| OPH-11B | 2.9 |
| OPH-12A | 5.1 |
| OPH-12B | 7.1 |
| OPH-12C | 5.6 |
| OPH-14 | 5.4 |
| OPH-15 | 6.4 |
| OPH-16A | 5.8 |
| OPH-16B | 6.9 |

The solution was stirred during testing in order to reduce external diffusion influences. Diffusion will be a more significant limitation in the immobilized enzyme compared to the whole cells from the fermenter because of immobilized cells particles are significantly larger than the whole cells and hence the paraoxon has to diffuse further to reach the enzyme in the center of the immobilized particles. It may also be possible to calculate the effect of the diffusion limitation but was not attempted in the present example. Reducing the particle size was also examined as a method to reduce the influence of diffusion in the immobilized particles.

Figure 2:
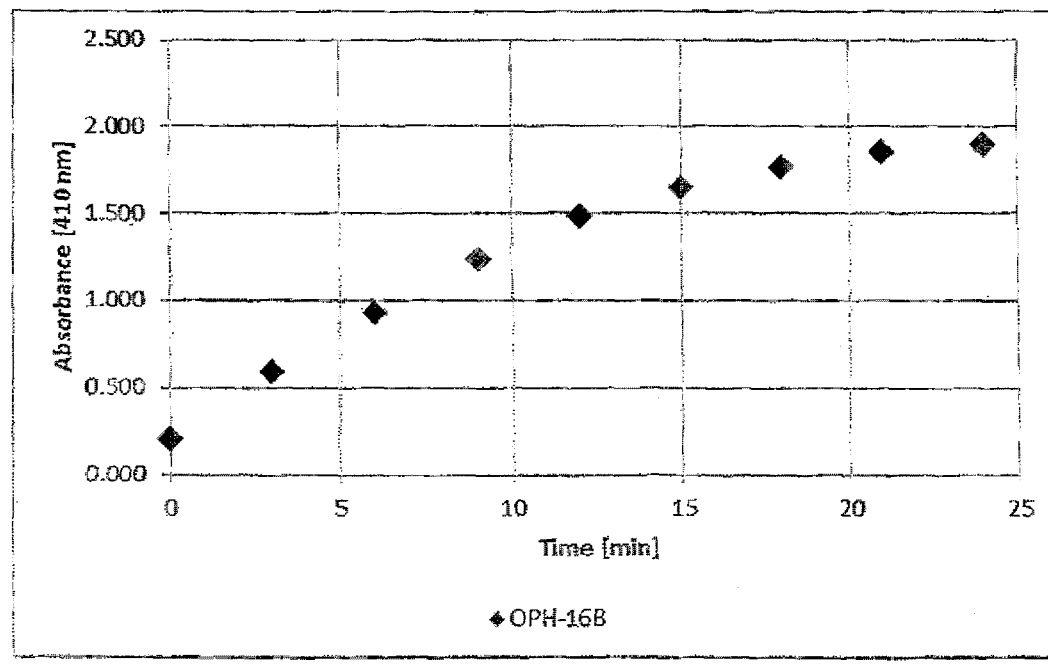
FIG. 2 is a graph showing absorbance vs. time data of OPH enzyme in an immobilized form.

FIGS. 1-2 show plots of absorbance vs. time for the whole cells from the fermentation and also for immobilized whole cells. It should be noted that the presence of whole cells and the immobilized particles suspended in solution interferes slightly with the absorbance even though most of the particles are settled before the absorbance was measured. The graphs shown in FIGS. 1-2 illustrate that a slower rate of reaction occurs with the immobilized cells. Vigorous mixing has improved the rate of reaction for the immobilized materials but better mixing conditions probably can be found.

Figure 8:
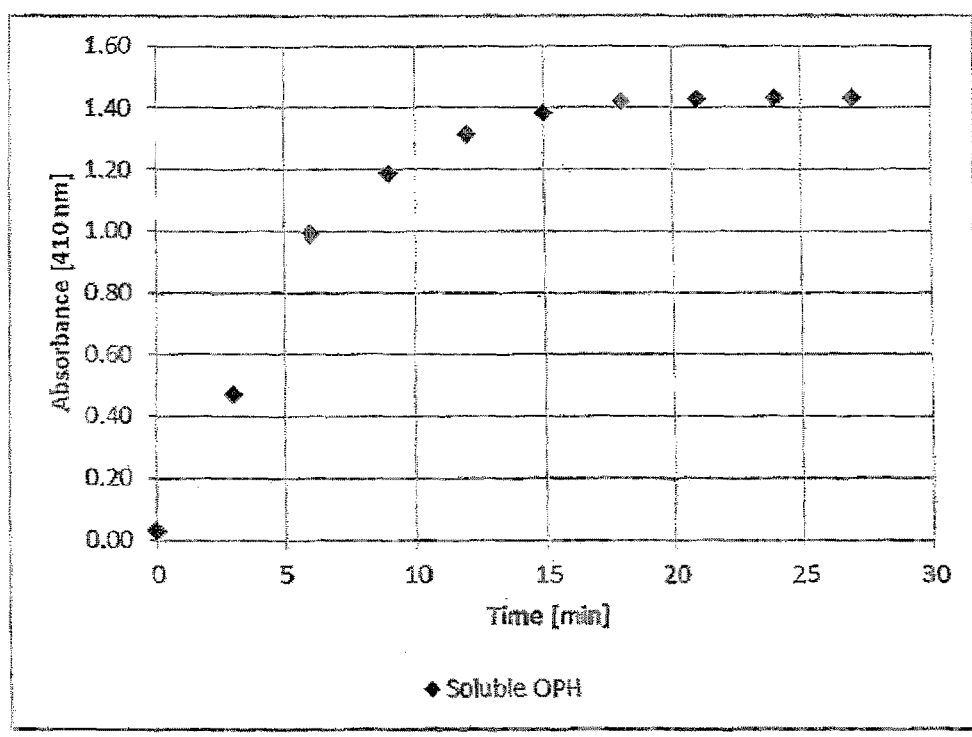
FIG. 8 is a graph showing absorbance vs. time data for soluble OPH enzyme.
Figure 9:
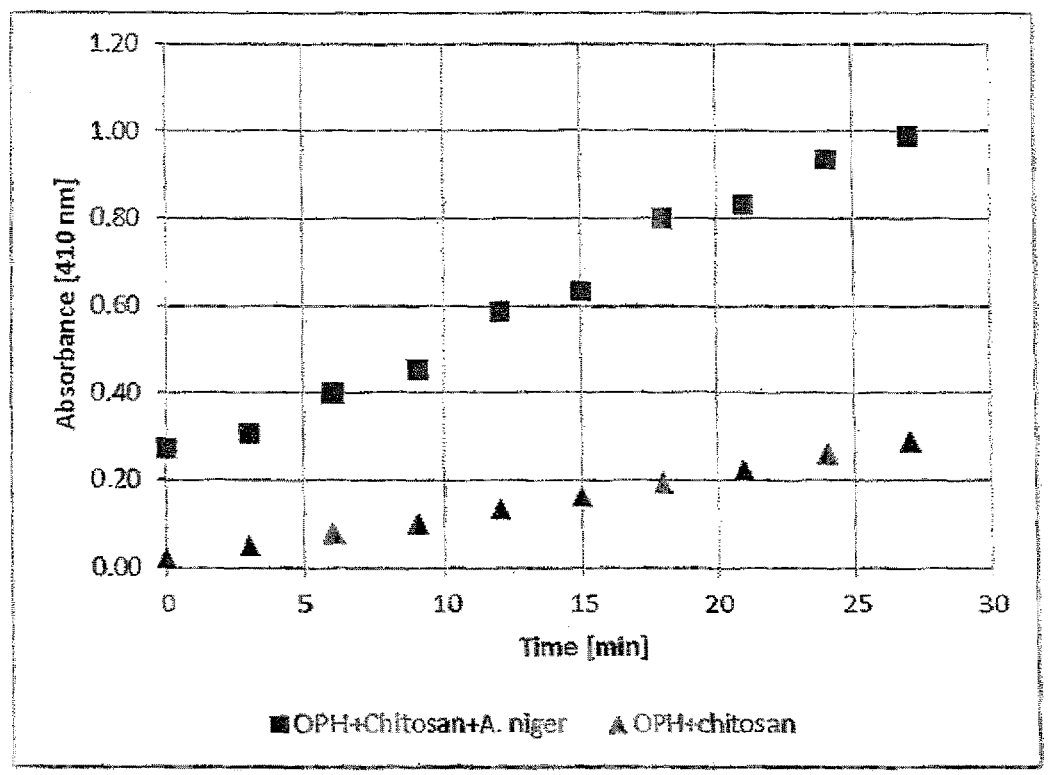
FIG. 9 is a graph showing absorbance vs. time data for immobilized forms of OPH enzymes.
Figure 10:
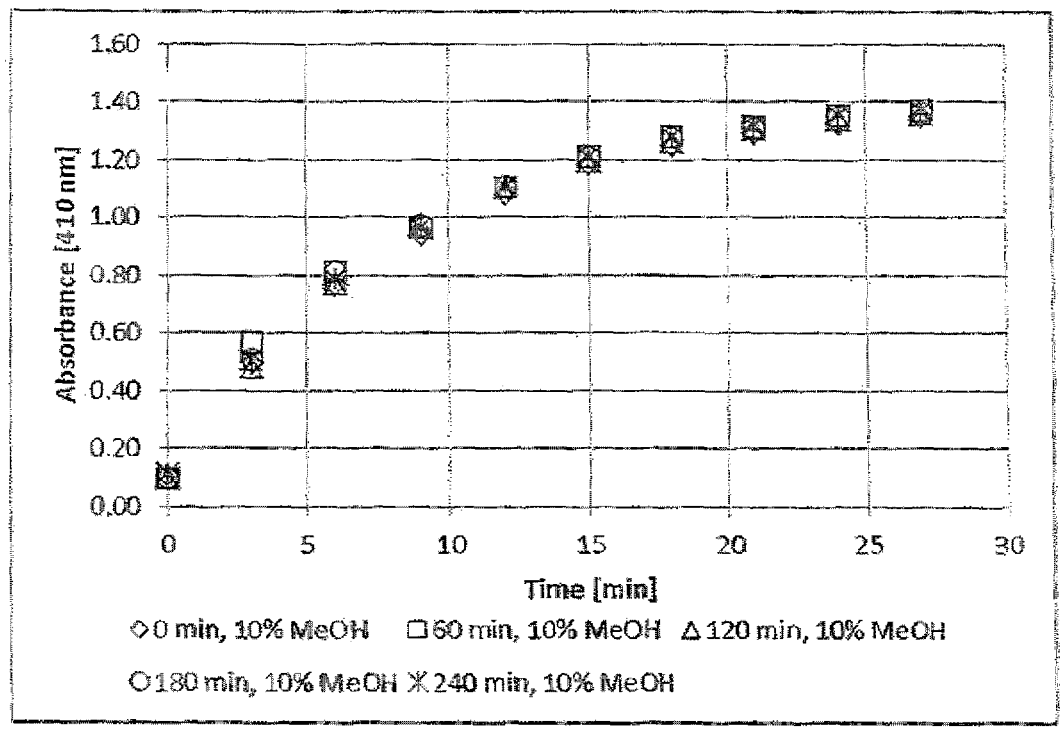
FIG. 10 is a graph showing absorbance vs. time data for OPH in a cell slurry in 10% methanol solution.
Figure 11:
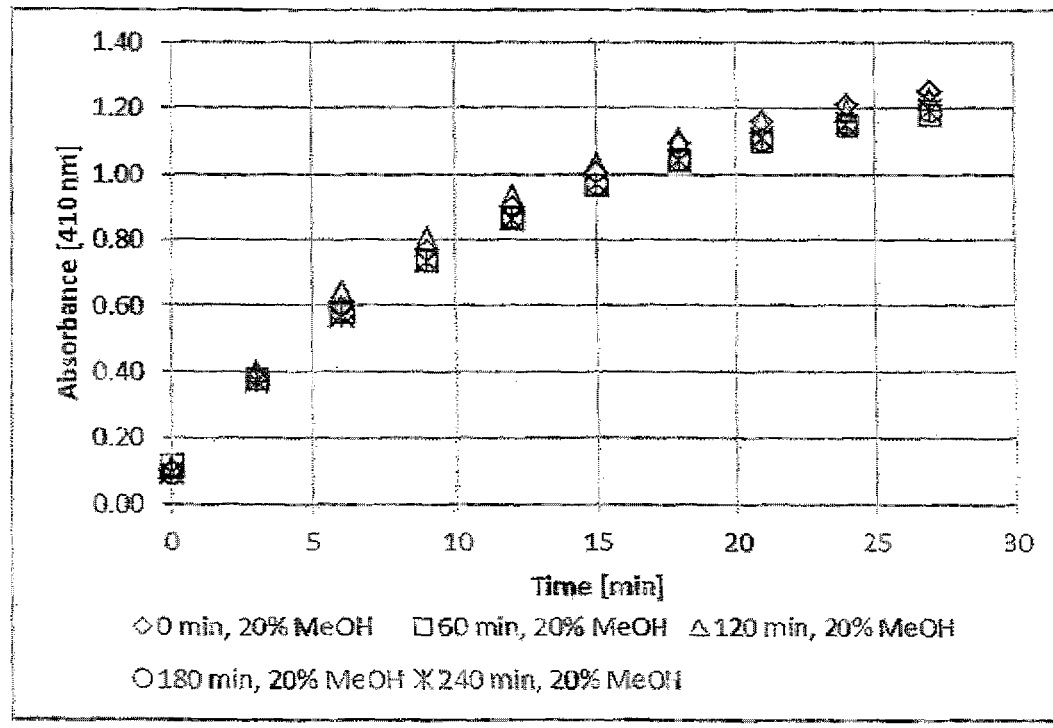
FIG. 11 is a graph showing absorbance vs. time data for OPH in a cell slurry in 20% methanol solution.
Figure 12:
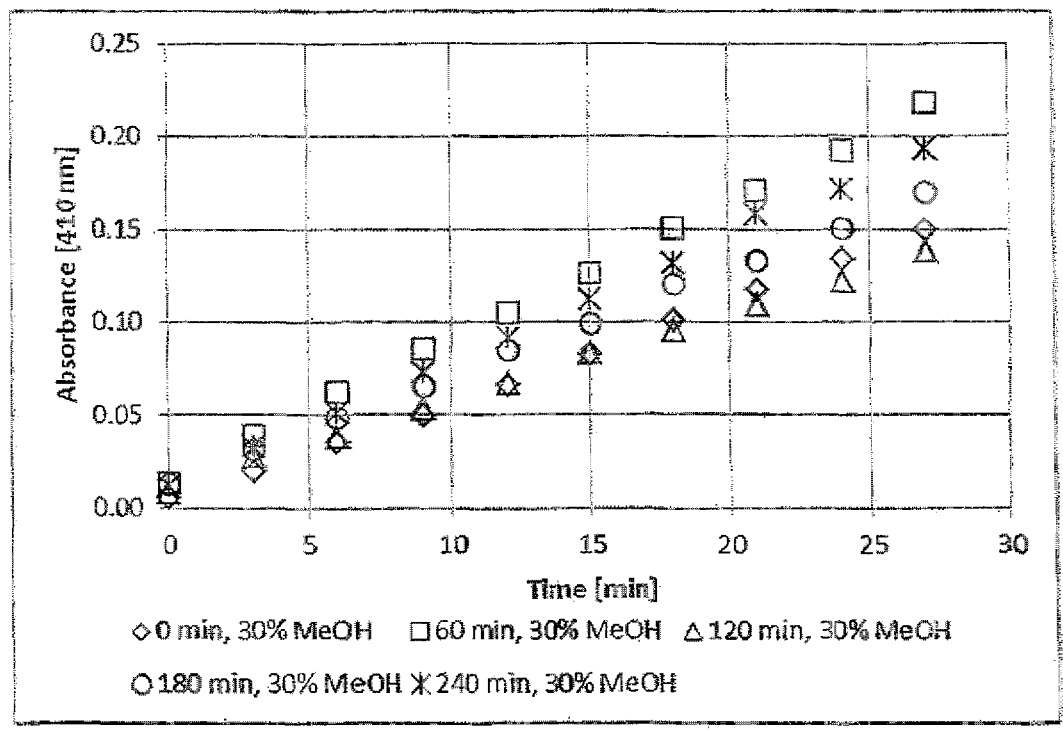
FIG. 12 is a graph showing absorbance vs. time data for OPH in a cell slurry in 30% methanol solution.
Figure 13:
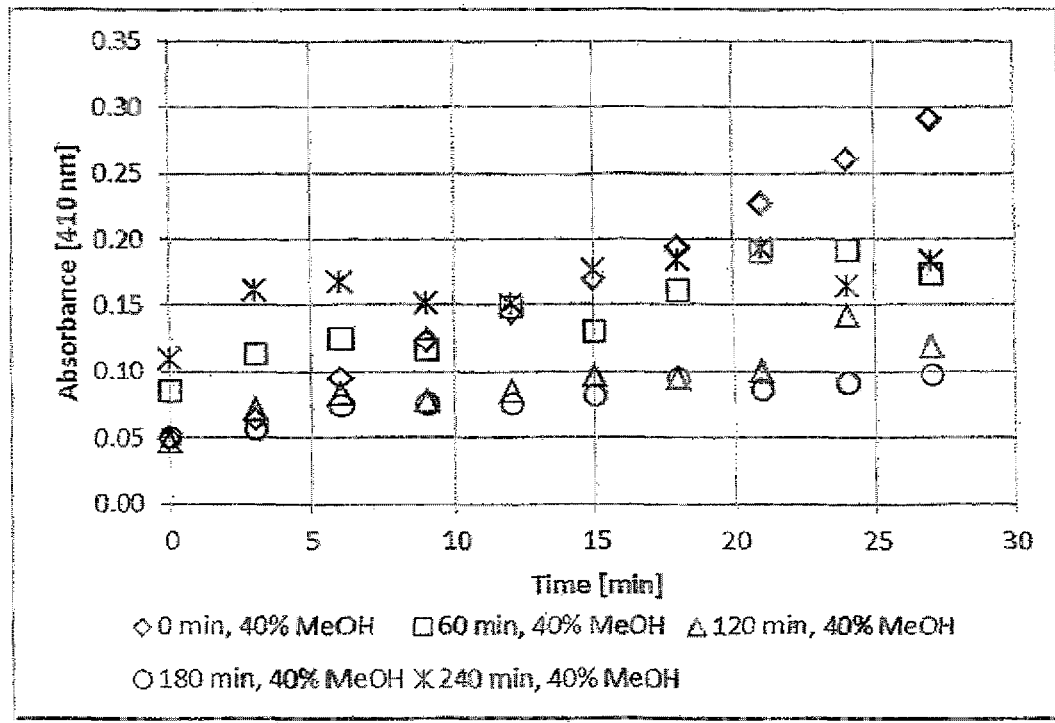
FIG. 13 is a graph showing absorbance vs. time data for OPH in a cell slurry in 40% methanol solution.
Figure 14:
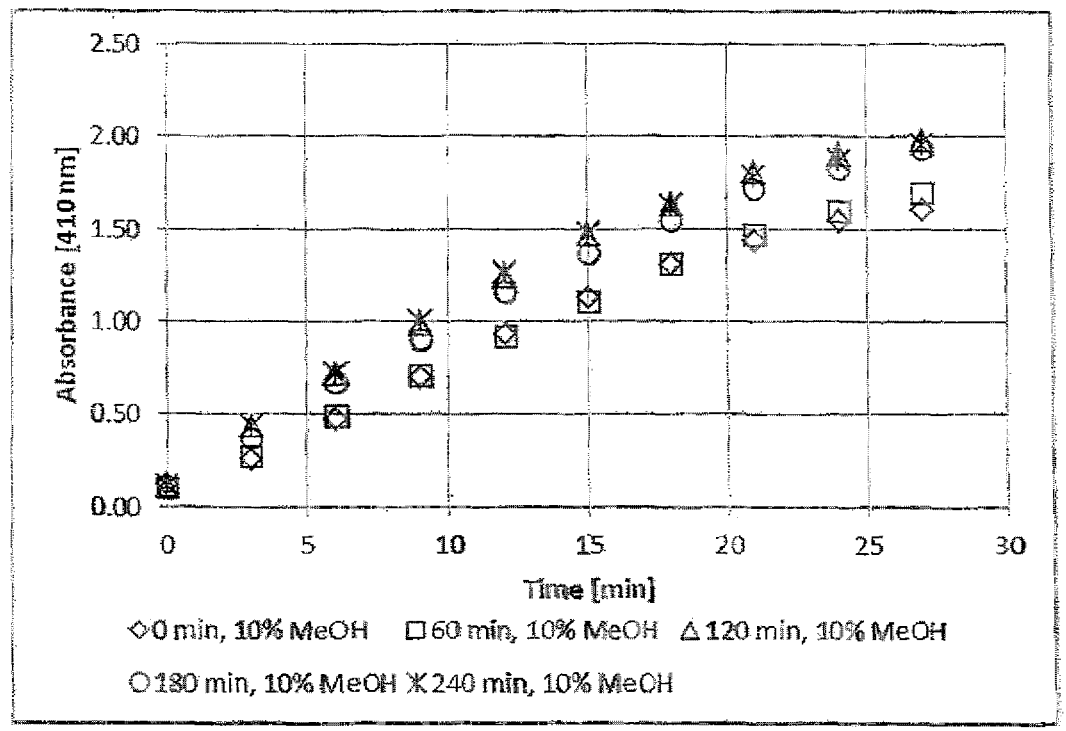
FIG. 14 is a graph showing absorbance vs. time for immobilized OPH in 10% methanol solution.
Figure 15:
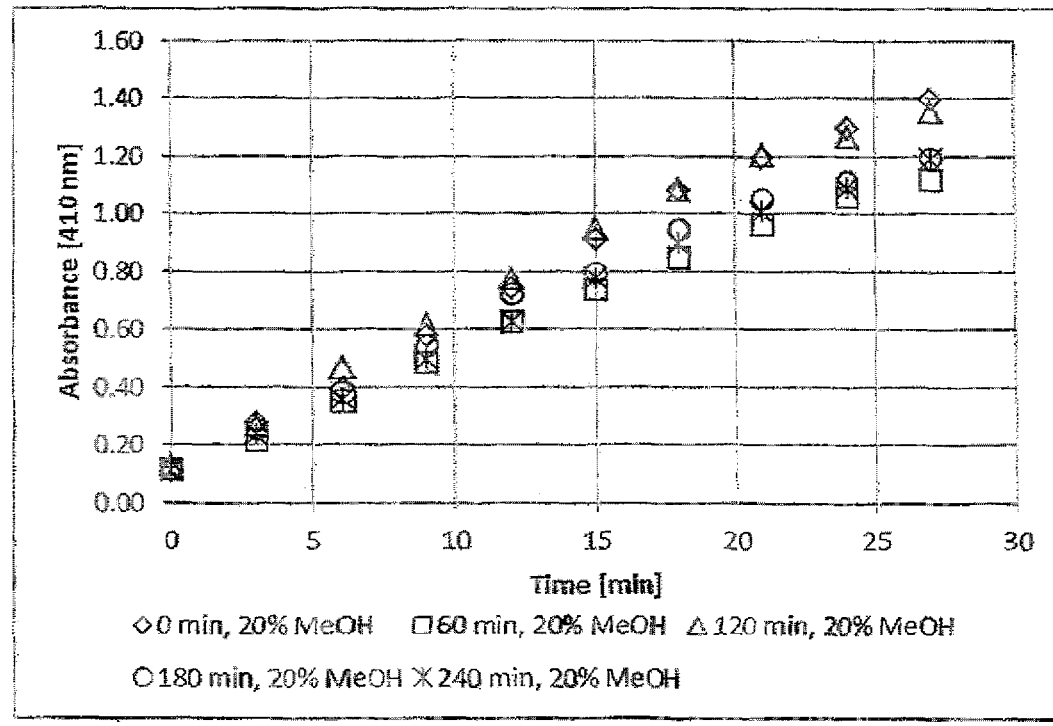
FIG. 15 is a graph showing absorbance vs. time for immobilized OPH in 20% methanol solution.
Figure 16:
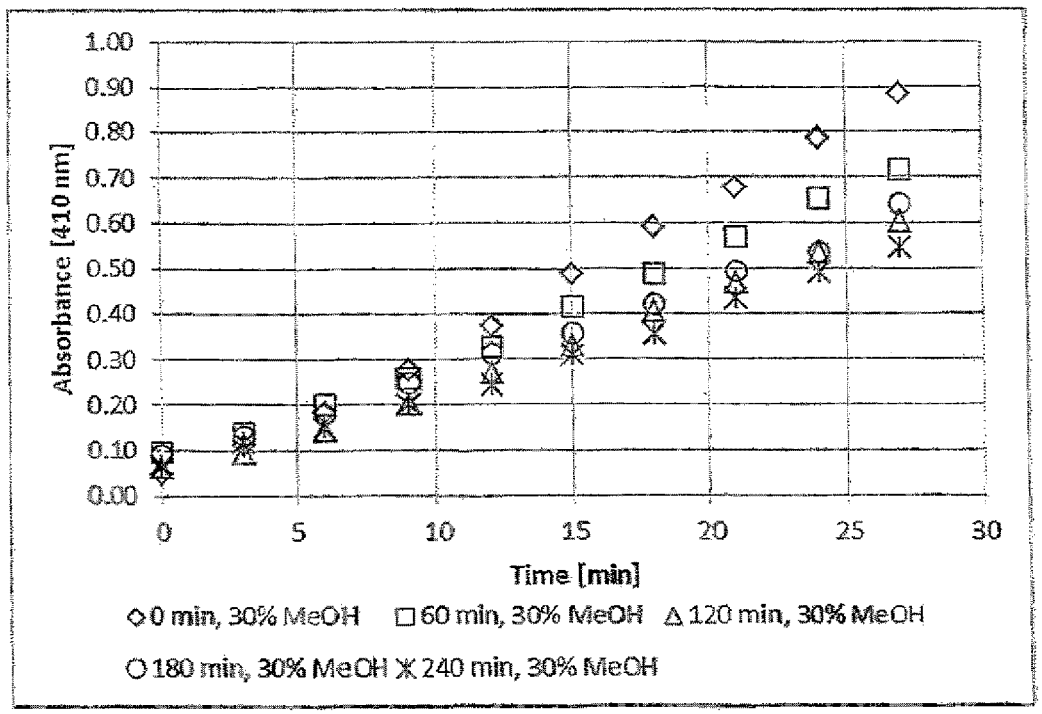
FIG. 16 is a graph showing absorbance vs. time for immobilized OPH in 30% methanol solution.
Figure 17:
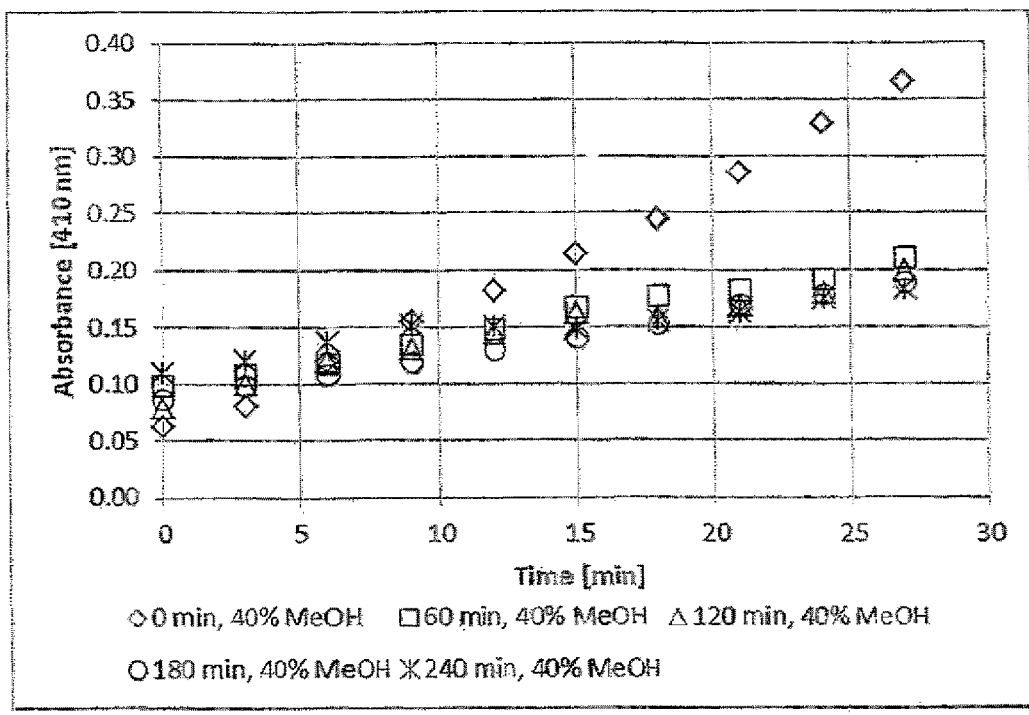
FIG. 17 is a graph showing absorbance vs. time for immobilized OPH in 40% methanol solution.
Figure 18:
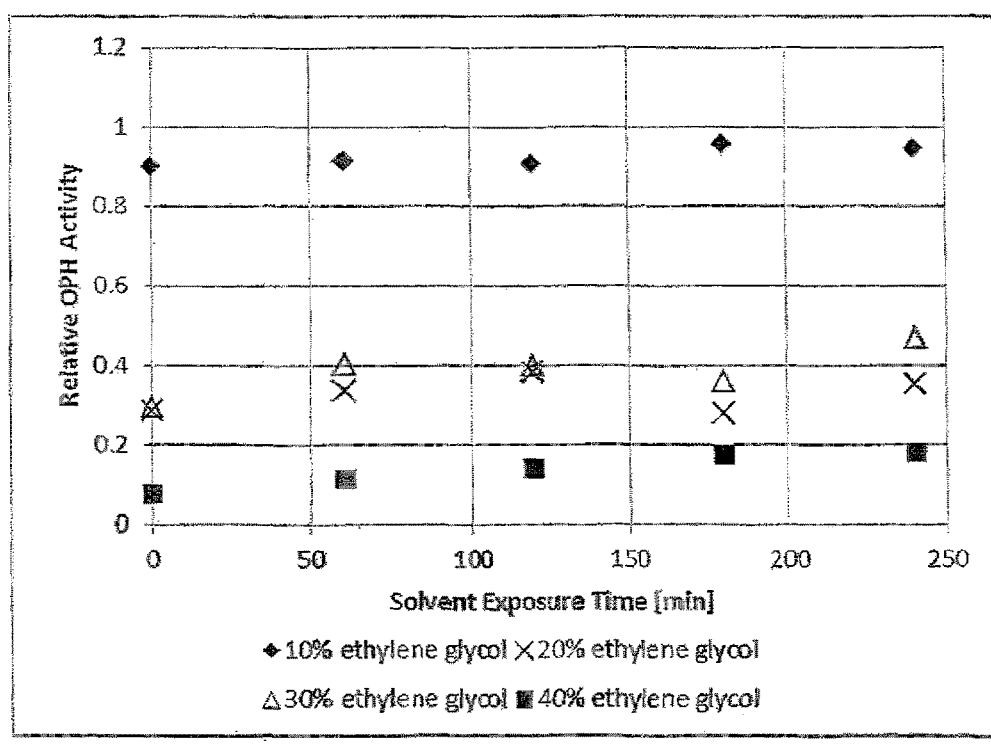
FIG. 18 is a graph showing the change in activity of free OPH enzyme over time with exposure to ethylene glycol solutions relative to its activity in a solvent-free solution.
Figure 19:
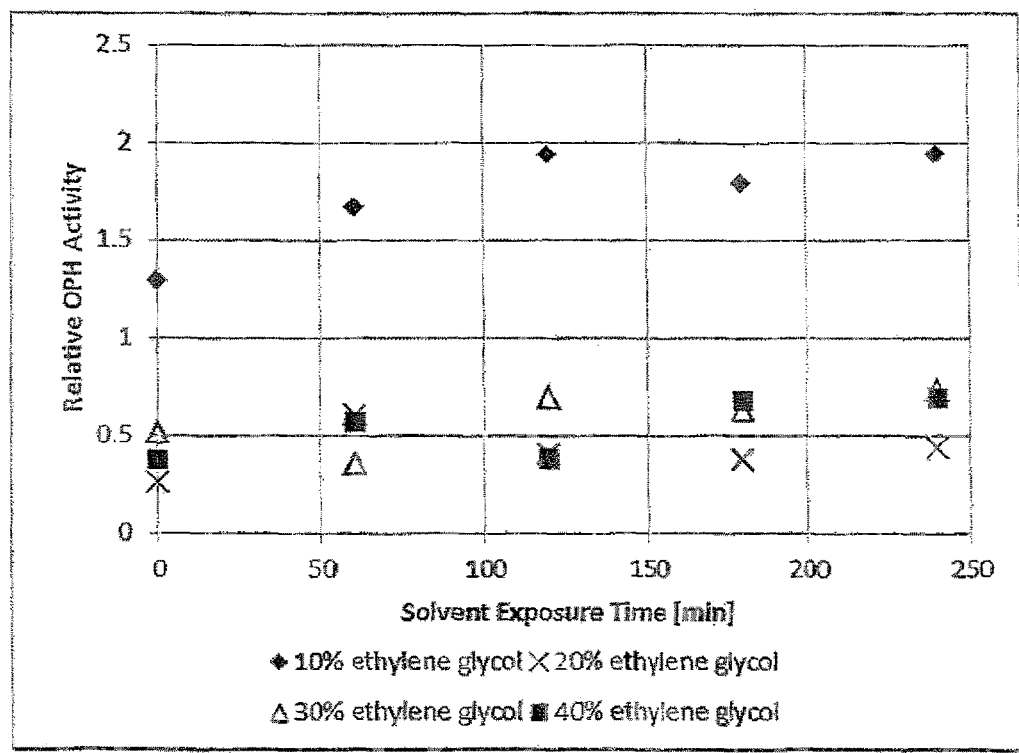
FIG. 19 is a graph showing the change in activity of the OPH-7 immobilized form of the OPH enzyme over time with exposure to ethylene glycol solutions relative to its activity in a solvent-free solution.
Figure 20:
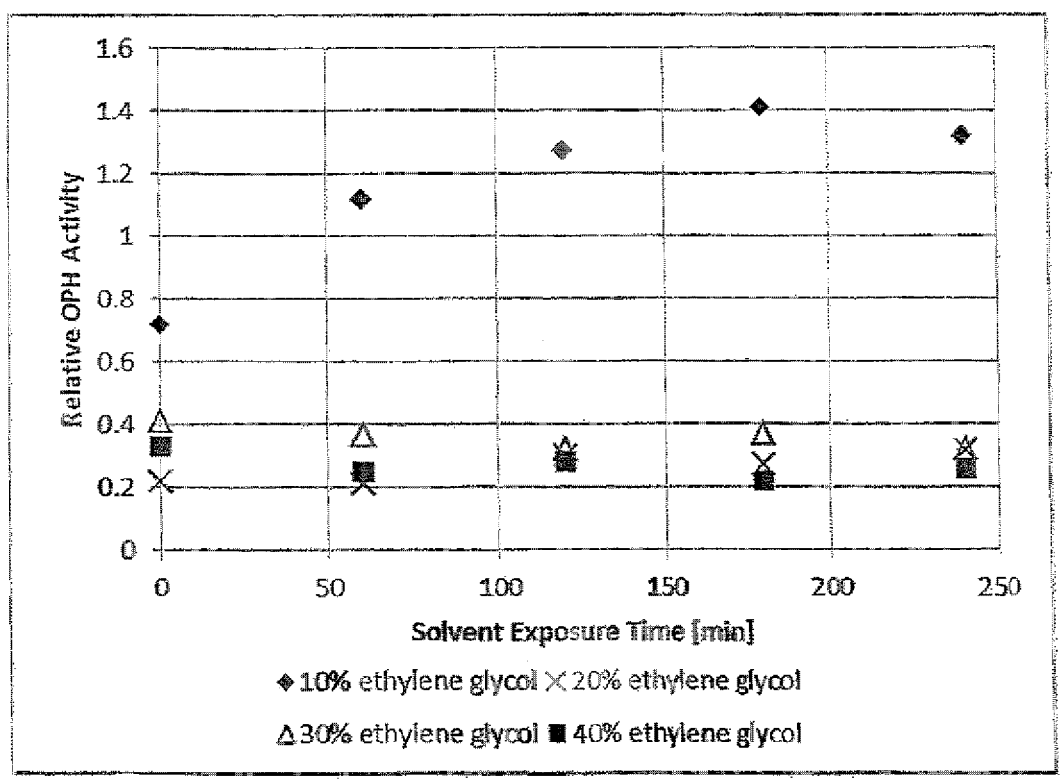
FIG. 20 is a graph showing the change in activity of the OPH-14 immobilized foam of the OPH enzyme over time with exposure to ethylene glycol solutions relative to its activity in a solvent-free solution.
Figure 21:
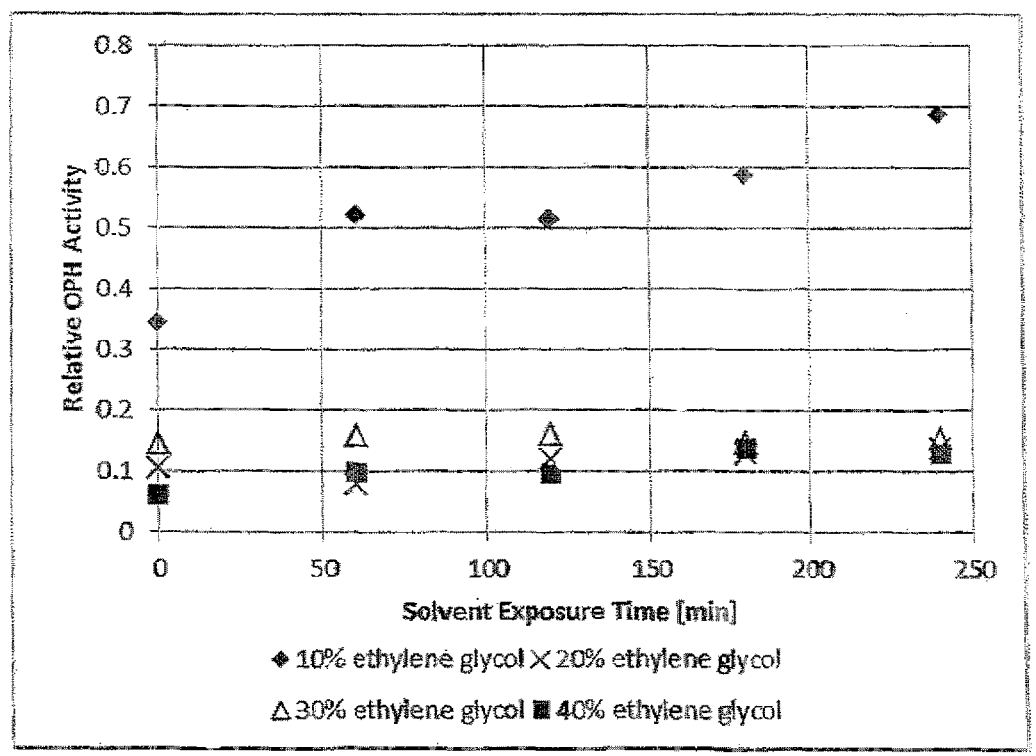
FIG. 21 is a graph showing the change in activity of the OPH-15 immobilized form of the OPH enzyme over time with exposure to ethylene glycol solutions relative to its activity in a solvent-free solution.

FIGS. 8-9 show two plots of absorbance vs. time for soluble OPH enzyme and also for variants of immobilized soluble enzyme. The assay for these solutions was the same as the one previously described for both free enzyme and immobilized enzyme. The graphs show that the biodegradable immobilized soluble enzyme can still accomplish the desired chemical conversion. The data also demonstrates that the chitosan and *A. niger* formulation has an improved activity compared to the chitosan only formulation as indicated by the higher reaction velocity.

Xylanase

Xylanases (XY) are enzymes that hydrolyse beta-1-4-xylane into xylose, thus breaking down the linear polysaccharide that makes up a significant portion of plant cell walls. The enzyme reaction has the following stoichiometry:

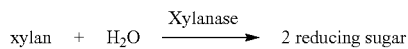

$$xylan + H_2O \xrightarrow{Xylanase} 2 \text{ reducing sugar}$$

Commercial applications for xylanase include uses in the papermaking process, as food additives in the processing of meats and breads, for the clarification of fruit juices, and it is being explored for use in the production of biofuel from plant material.

A colorimetric assay for evaluating the activity of xylanase involves converting xylan in a buffer solution at pH 4.5 at 37° C. for one hour. Following this reaction a sample is taken from the reaction solution and the reducing sugars produced by the enzymatic reaction are further reacted with p-hydroxybenzoic acid hydrazide (PAHBAH) in a boiling alkaline solution which reacts with the reducing sugars to form a product that adsorbs at 410 nm. This absorbance can be compared to that from a standard curve for reducing sugars and the activity of the xylanase can be calculated. Thus the enzyme's activity can be determined by the amount of xylan converted to xylose (reported as (units/g) Xylanase enzyme). It was noted that the presence of *Aspergillus niger* mycelium appeared to elevate the xylose readings. Immobilized enzymes had a particle size of about 200 μm. Table 2 provides the enzyme's activity ((units/g) immobilized Xylanase enzyme). Other commonly accepted methods for determining enzyme activity could also be used.

TABLE 2

| | Activity [units/g xylanase] |
|---|---|
| XY-1 | 37.2 |
| XY-2 | 31.6 |
| XY-3 | 20.1 |
| XY-4 | 12.6 |
| XY-5 | 9.8 |

Alcohol Dehydrogenase

Alcohol dehydrogenases (ADH) are oxidoreductase enzymes that facilitate the interconversion between a broad range of alcohols and aldehydes or ketones with the reduction of nicotinamide adenine dinucleotide (β-NAD⁺ to β-NADH). The enzyme reaction has the following stoichiometry:

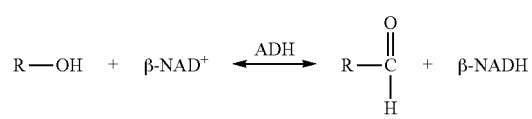

where R represents alkyl groups although optionally the alcohol involved is either a primary or secondary alcohol, or a hemi-acetals. ADH plays a role in the fermentation of alcohols by yeast and bacteria and is key in the processing of ethanol in humans.

The activity of the enzyme may be defined by the conversion of ethanol to acetaldehyde. The assay for ADH was performed in which stirred 12 mL assay solutions with 10-100 mg of immobilized enzyme or serial dilutions of 1 mg/mL enzyme stock solutions. The standard assay solution consisted of a 50 mM sodium pyrophosphate buffer, 25% ethanol (v/v), and 4 mM β-NAD⁺ at a pH of 8.8. The velocity of the enzyme reaction is determined by sampling the assay solution every 2 minutes and measuring the absorbance at 340 nm (corresponding to the concentration of β-NADH).

The enzyme's activity was determined by the amount of β-NAD⁺ converted to β-NADH (reported as units/g alcohol dehydrogenase enzyme). One unit converts 1.0 μmole of ethanol to acetaldehyde per minute at pH 8.8 at 25° C. Immobilized enzymes had a particle size of about 200 μm. Table 3 provides the enzyme's activity. Other commonly accepted methods for determining enzyme activity could also be used.

TABLE 3

| | Activity [units/g alcohol dehydrogenase] |
|---|---|
| AD-1 | 52.8 |
| AD-2 | 93.3 |
| AD-3 | 27.6 |
| AD-4 | 37.2 |
| AD-5 | 27.3 |

Pyruvate Decarboxylase

Pyruvate decarboxylase (PDC) is a homotetrameric lyase (EC 4.1.1.1) that catalyzes the decarboxylation of pyruvic acid to acetaldehyde and carbon dioxide. The enzyme reaction follows the stoichiometry below:

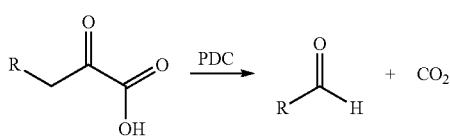

where R is a representative alkyl group. PDC plays a significant role in the anaerobic fermentation process in yeast.

The assay used to determine the activity of the PDC utilized an indirect method in which the conversion of pyruvate to acetaldehyde is linked to the activity of ADH, which is provided in excess, and converts the acetaldehyde into β-NAD⁺ and ethanol. The reaction is monitored at 340 nm, which corresponds to the consumption of β-NADH upon the formation of acetaldehyde through the ADH driven reaction. For the assay an immobilized enzyme sample (~10 milligrams) is added to a 12 mL solution at pH 6.0 containing 200 mM citrate buffer, 34 mM sodium pyruvate, 0.1 mM NAD⁺, and 35 U/mL of ADH. The velocity of the enzyme reaction is determined by sampling the sampling the assay solution and measuring the absorbance at 340 nm every 3 minutes. The enzyme's activity was determined by the amount of β-NADH converted to β-NAD (reported as (units/g pyruvate decarboxylase enzyme)). One unit converts 1.0 μmole of pyruvate to acetaldehyde per minute at pH 6.0 at 25° C. Immobilized enzymes had a particle size of about 200 μm. Table 4 provides the enzyme's activity. Other commonly accepted methods for determining enzyme activity could also be used.

TABLE 4

| | Activity [units/g pyruvate decarboxylase] |
|---|---|
| PDC-1 | 97.6 |
| PDC-2 | 0.00 |
| PDC-3 | 78.7 |
| PDC-4 | 87.8 |
| PDC-5 | 18.6 |
| PDC-6 | 20.2 |

Peroxidase

Peroxidases (PO) are a large family of enzymes that may catalyze the following reaction:

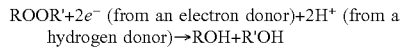

where R and R' are from a wide variety of alkyl groups. For many of these enzymes the optimal electron donor is hydrogen peroxide, but others have been shown to be more active with donors such as lipid peroxides. POs can be used industrially for the treatment of industrial wastewater and are being explored as an alternative to a number of harsh chemicals that complicate manufacturing processes for adhesives, computer chips, and linings.

Peroxidase from horseradish was utilized in the case of these examples. The assay uses 4-aminoantipyrine as the hydrogen donor and hydrogen peroxide as the electron donor. The assay solution consists of 0.1 M potassium phosphate buffer, 0.85 mM hydrogen peroxide, 1.25 mM 4-aminoantipyrine, and 85 mM phenol at a pH of 7.0.

An immobilized enzyme sample (10 milligrams) was added to the substrate solution (and stirred. The velocity of the reaction is monitored through sampling the assay solution and monitoring the change in absorbance every 2 minutes at 510 nm as the reaction progresses. The enzyme's activity was determined by the decomposition of hydrogen peroxide (reported as (units/mg peroxidase enzyme)). One unit results in the decomposition of 1.0 μmole of hydrogen peroxide per minute at pH 7.0 at 25° C. Immobilized enzymes had a particle size of about 200 μm. Table 5 provides the enzyme's activity. Other commonly accepted methods for determining enzyme activity could also be used.

TABLE 5

| | Activity [units/mg peroxidase] |
|---|---|
| PO-1 | 9.7 |
| PO-2 | 4.8 |
| PO-3 | 19.3 |
| PO-4 | 3.5 |
| PO-5 | 6.1 |
| PO-6 | 3.6 |
| PO-7 | 1.9 |
| PO-8 | 9.2 |
| PO-9 | 2.9 |
| PO-10 | 2.3 |

Enzyme Thermal Stability Testing

Many enzymes may lose activity over time and especially when the temperature is elevated. Thermal stability is important for storage and/or usage when the enzyme can be exposed to higher temperatures. Enzymes were immobilized according to the process described above and used in the thermal stability tests. Determination of the long-term storage stability under heated conditions of free and immobilized enzyme was made by exposing test tubes containing enzyme to 52.5° C., 65° C., and 70° C. environments for periods from 30 minutes to 24 hours. Additionally effects on reactive pot-life can be determined by a similar test, the difference being that the enzyme material is mixed in a substrate-free version of the assay solution during the heat exposure. For all evaluations, following exposure to heat the material was cooled in an ice bath for 10 minutes before the assay was run at room temperature.

Storage Temperature Testing

Figure 3:
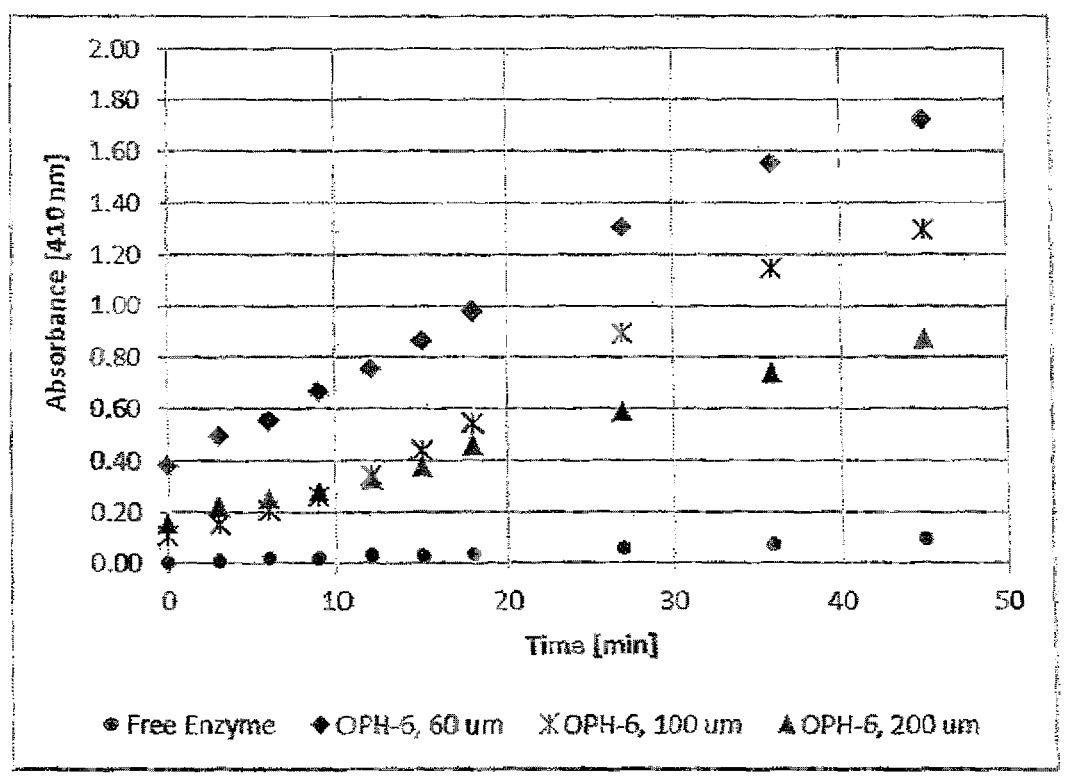
FIG. 3 is a graph showing absorbance vs. time data for OPH enzyme in cell slurry and in immobilized forms with different particle sizes after exposure to 52.5° C. temperature for four hours.

The graph shown in FIG. 3 shows the absorbance as a function of time for different samples exposed to 52.5° C. for four hours. These samples represent immobilized OPH samples at three different particle sizes and one free enzyme sample. It can be seen that the non-immobilized whole cell enzyme ("Free Enzyme" in the figure) has lost most of its activity after four hours of exposure to 52.5° C. temperature whereas the immobilized enzyme ("OPH" in the graph) retained significant activity. It can also be seen that the smaller sized particles give greater activity as might be expected based upon mass transfer considerations.

Figure 7A:
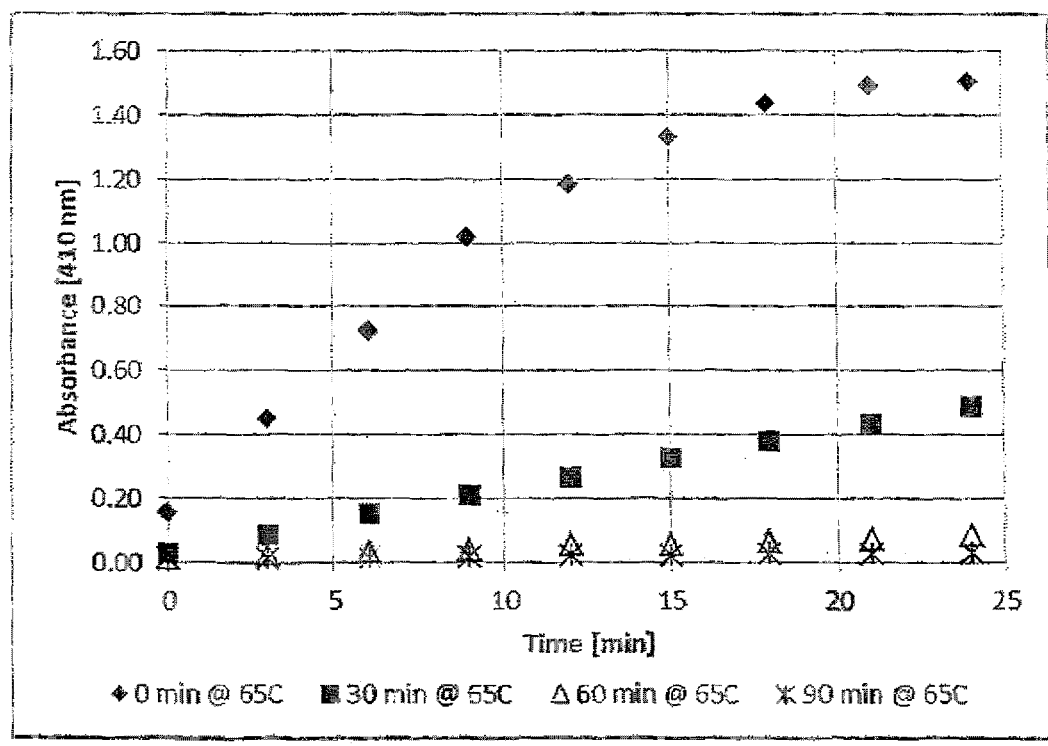
FIG. 7A is a graph showing absorbance vs. time data for OPH in a cell slurry after various amounts of time exposed to 65° C.
Figure 7B:
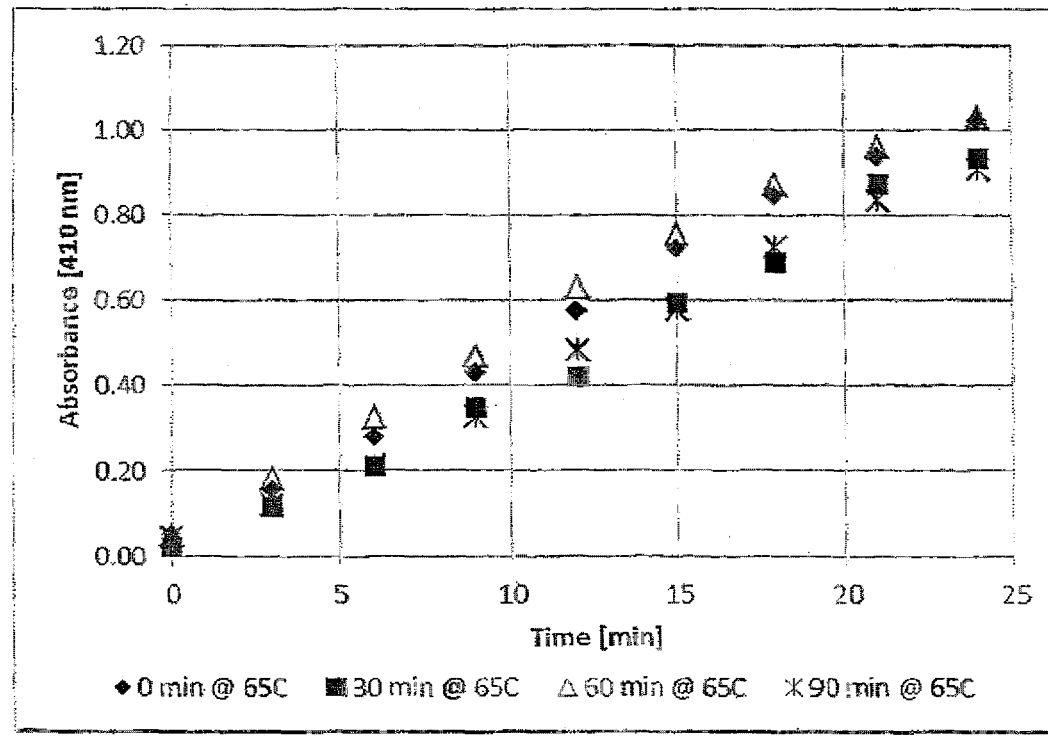
FIG. 7B is a graph showing absorbance vs. time data for an immobilized form of OPH after various amounts of time exposed to 65° C.
Figure 22A:
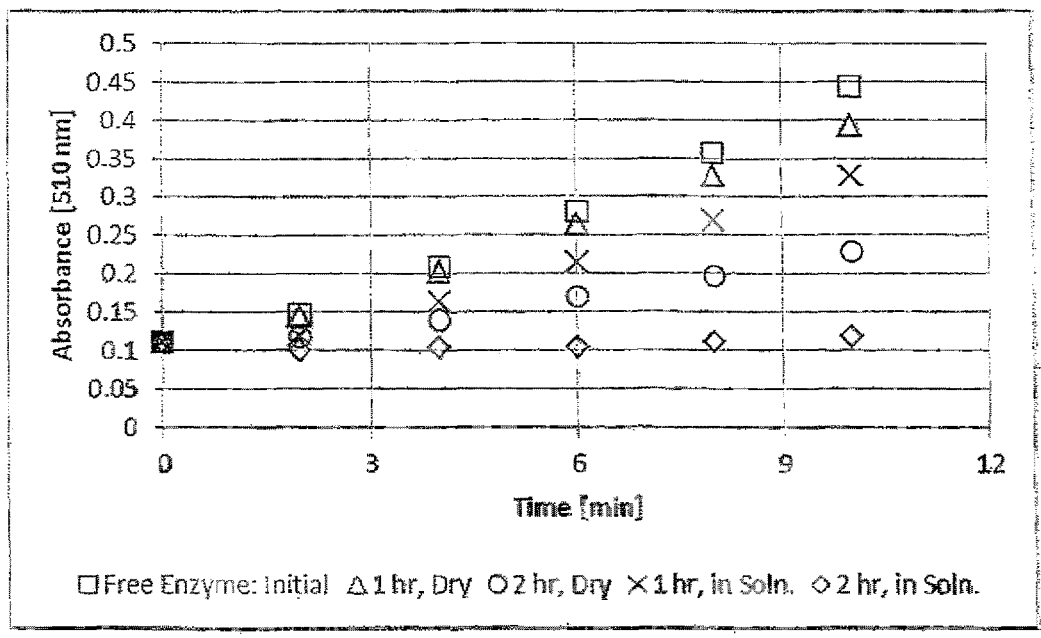
FIG. 22A is a graph showing absorbance vs. time data for Free PO after various amounts of time exposed to 65° C. as either dry crystals or as suspended in buffer solution.
Figure 22B:
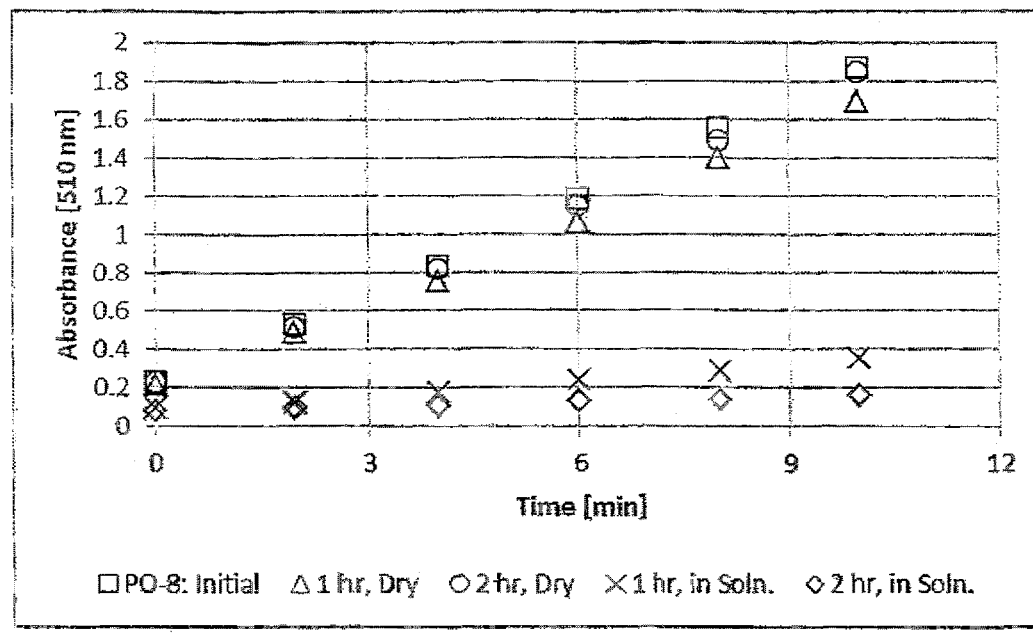
FIG. 22B is a graph showing absorbance vs. time data for an immobilized form of PO after various amounts of time exposed to 65° C. either as a dry powder or suspended in a buffer solution.

Immobilized forms of OPH enzyme were tested for activity after being subjected to 65° C. for various periods of time. The results of this experiment are shown in FIGS. 7A and 7B. Similarly FIGS. 22A and 22B show the activity of PO in both immobilized and free enzyme forms after exposure to 65° C. for similar time periods. The data demonstrates that this chitosan formulation has good temperature stability, similar to the PEI formulation.

The specific activity of enzyme material exposed to 65° C. for 0-120 minutes was further explores as a means to simulate the storage stability of the immobilized enzyme and the change in activity (relative to the activity of untreated material) with time at elevated temperature is provided in Tables 6 A-C. Noteworthy is that the immobilization process appears to increase the activity of the enzyme after exposure to elevated temperature. The presence of an increase in activity and its degree appear to be related to the formulation.

TABLE 6A

|  | Time at 65° C. | | | |
| --- | --- | --- | --- | --- |
|  | 30 min | 60 min | 90 min | 120 min |
| Enzyme/Cell Slurry | −79.1% | −98.1% | −99.2% | −99.8% |
| OPH-5 | −27.4% | −39.7% | −22.4% | −18.8% |
| OPH-6 | +24.1% | −9.6% | +14.1% | −16.6% |
| OPH-7 | −10.5% | +0.9% | −10.5% | +20.3% |
| OPH-8 | −5.2% | −14.9% | −11.1% | −2.3% |
| OPH-9A | — | +0.4% | — | +8.3% |
| OPH-9B | — | +17.0% | — | +34.7% |
| OPH-12B | — | +2.1% | — | −1.4% |
| OPH-16B | — | −8.3% | — | −1.0% |

TABLE 6B

|  | Time at 65° C. | |
| --- | --- | --- |
|  | 60 min | 120 min |
| Free XY Enzyme | −0.7% | +21.2% |
| XY-1 | +31.8% | +16.0% |
| XY-2 | +3.1% | −35.6% |

TABLE 6C

|  | Time at 65° C. | |
| --- | --- | --- |
|  | 60 min | 120 min |
| Free PO Enzyme | −7.5% | −48.0% |
| PO-1 | +22.8% | −69.3% |
| PO-3 | −66.7% | −63.2% |
| PO-8 | −10.5% | −2.4% |

Operational Temperature Testing

The relative decrease in specific activity, referenced to the unexposed condition, of OPH (units/mg) of material exposed to 65° C. in 10% assay solution for 0-120 min simulates operational half-life, and is provided in Tables 7 A-C. This data can be used to determine the extension of the enzyme's reactive half-life from immobilization, and its extent is dependent on the immobilization process and formulation.

TABLE 7A

|  | Time at 65° C. | |
| --- | --- | --- |
|  | 60 min | 120 min |
| Enzyme/Cell Slurry | −92.0% | −98.2% |
| OPH-6 | −79.8% | −80.3% |
| OPH-7 | −52.6% | −77.9% |
| OPH-9A | −95.2% | −93.0% |
| OPH-9B | −84.6% | −85.3% |
| OPH-12B | −53.6% | −73.6% |
| OPH-14 | −26.9% | −45.7% |
| OPH-15 | −68.9% | −80.9% |
| OPH-16B | −74.3% | −86.6% |

TABLE 7B

|  | Time at 65° C. | |
| --- | --- | --- |
|  | 60 min | 120 min |
| Free Enzyme | −54.2% | −38.4% |
| XY-1 | −23.2% | −24.2% |
| XY-2 | +110.8% | −38.8% |

TABLE 7C

|  | Time at 65° C. | |
| --- | --- | --- |
|  | 60 min | 120 min |
| Free PO Enzyme | −49.1% | −91.8% |
| PO-1 | −85.4% | −80.5% |
| PO-3 | −70.1% | −83.1% |
| PO-8 | −84.2% | −95.4% |

Immobilized Enzyme Solvent Stability Testing

Many enzymes require the presence of water for activity in both the case where water is a component in the reaction (e.g. OPH catalyzed hydrolysis) and it can be involved in the enzyme configuration in its active state. However, enzyme activity is desirable on some chemicals that are sparingly soluble in water but more soluble in solvent-water mixtures. Therefore, it would be useful if enzyme activity could be maintained in such solvents. Herein tests were performed measuring the immobilized enzyme activity and immobilized activity in a variety of solvent-water solutions.

Isopropanol-Water Solution Stability

The enzyme's specific activity (units/mg) was initially studied in isopropanol/water solutions (10%, 20%) to determine the enzyme stability in water-soluble solvent solutions. The change in specific activity of the free and immobilized enzyme with exposure to isopropanol mixtures is provided in Table 8, below. The percent change is referenced to the activity of the sample in a 100% water solution.

TABLE 8

|  | % isopropanol | |
| --- | --- | --- |
|  | 10% | 20% |
| Enzyme/cell Slurry | −69.6% | −90.3% |
| OPH-7 | −19.8% | −56.5% |
| OPH-14 | −32.4% | −70.0% |
| OPH-15 | −61.7% | −84.4% |

From this data it appears that the immobilization process does grant some resistance to the denaturing action of the isopropanol compared to the change in the activity of the free enzyme.

Methanol-Water Solution Stability

Following up on the initial isopropanol testing, the enzyme's specific activity in methanol/water solutions (0%, 10%, and 20% methanol) was studied and the results are provided are reported as the change in activity referenced to the activity of the material in a 100% water solution in Table 9, below. This data shows that the performance of the immobilized enzyme is related to the steps in the immobilization process.

TABLE 9

|  | 10% Methanol | 20% Methanol |
|---|---|---|
| Free Enzyme/Cell Slurry | −22.9% | −78.9% |
| OPH-4 | −16.9% | −37.2% |
| OPH-5 | −91.8% | −88.7% |
| OPH-6 | −83.2% | −54.8% |
| OPH-8 | −67.7% | −92.6% |

Figure 4:
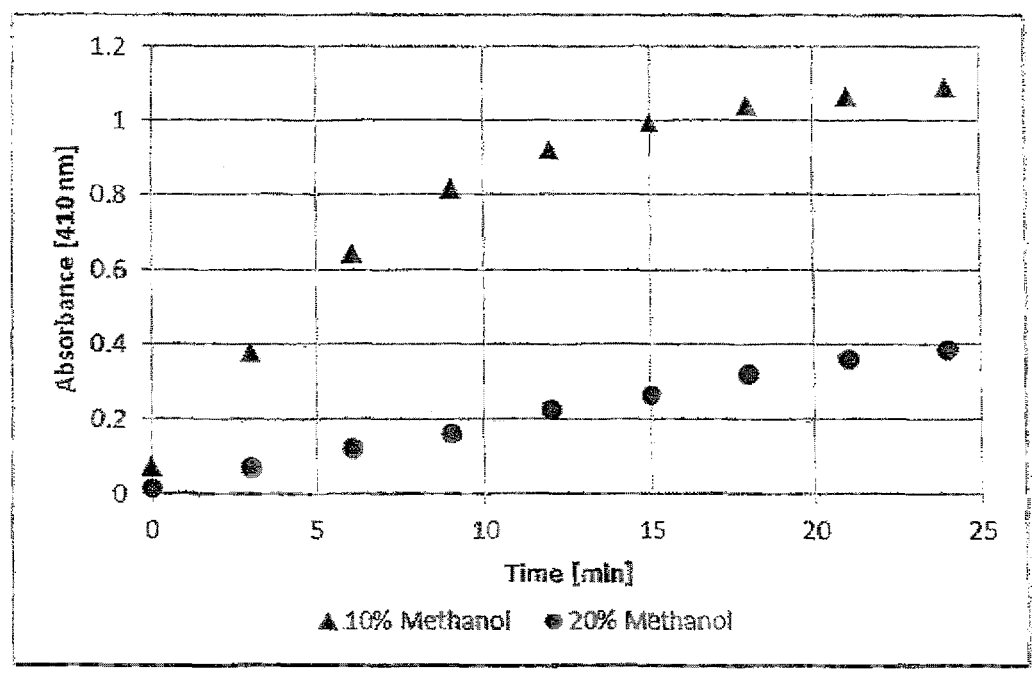
FIG. 4 is a graph showing absorbance vs. time for OPH in a cell slurry in methanol solutions.
Figure 5:
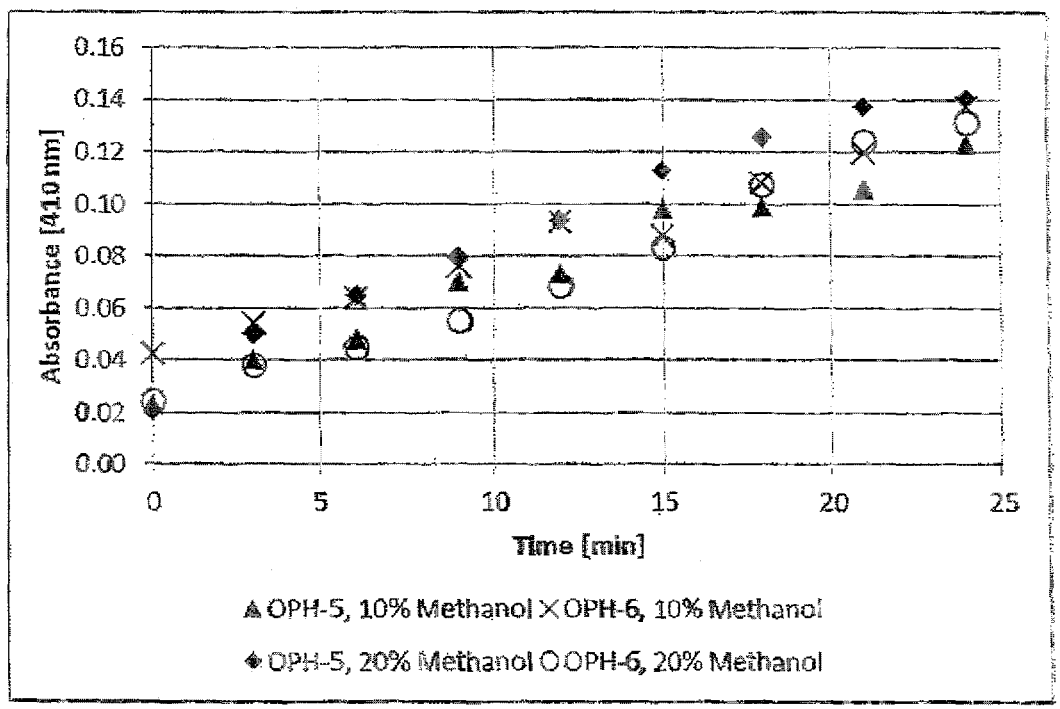
FIG. 5 is a graph showing absorbance vs. time for forms of immobilized OPH in methanol solutions.

The absorbance vs. time for these experiments is shown in FIG. 4. As can be seen in the graph, the activity for the free enzyme in 20% methanol is significantly reduced compared to the activity in 10% methanol. The graph shown in FIG. 5 shows the absorbance vs. time for two different immobilizations, OPH-5 and OPH-6. These particles were screened with a 30×30 mesh which provided particles of ~200 μm equivalent diameter. It can be seen that the activity of the OPH-5 immobilized enzyme in the 10% and 20% methanol solution was fairly equivalent. In other words, increasing the methanol concentration in the solution did not reduce the enzyme activity of this immobilized enzyme.

Figure 6:
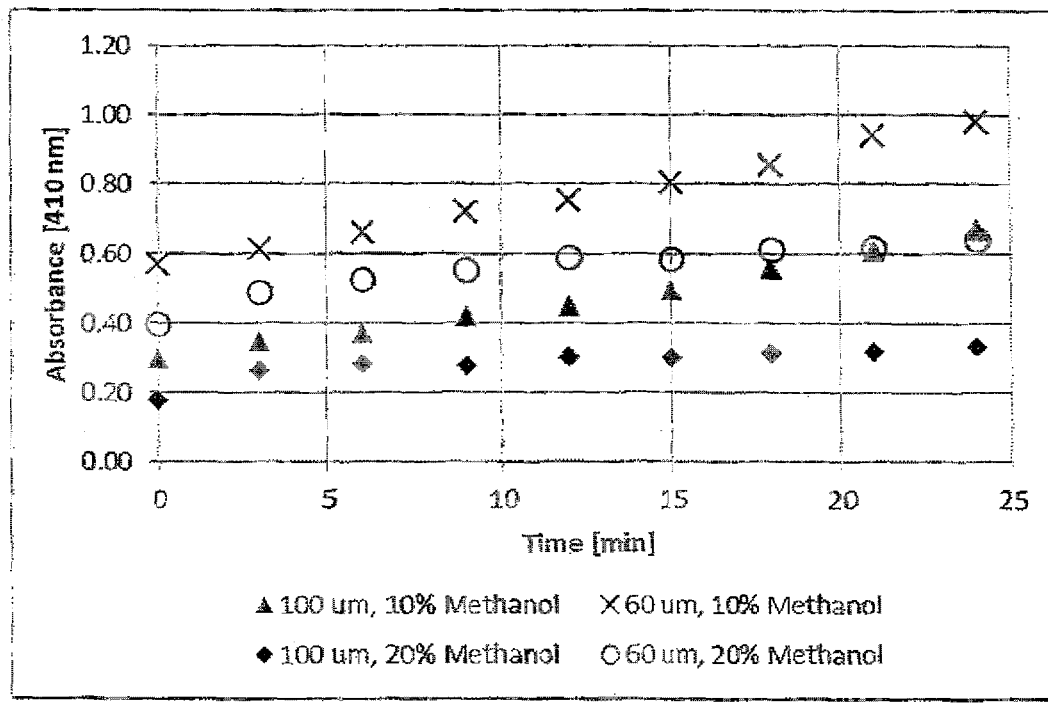
FIG. 6 is a graph showing absorbance vs. time for forms of immobilized OPH with different particle sizes in methanol solutions.

The same experiments were performed with immobilization experiments OPH-8 and OPH-6. These two immobilized enzymes were screened through two different sizes meshes. The OPH-8 was ground to a particle size of about 100 μm and the OPH-6 was ground to a size of roughly 60 μm diameter. The results of the experiment are shown in FIG. 6. It can be seen that increasing the methanol concentration from 10% to 20% reduces the activity for the larger particles to a greater degree.

A variation on the experiments was performed as it was desired to determine whether the activity of the enzyme would be reduced by continuous exposure to solvent over time. These experiments were performed with whole cell concentrates and immobilized particles screened with a 30×30 mesh from the OPH-7 immobilization. The activity assay performed is similar to the previous testing, except for this testing the enzyme containing material was preexposed to 1.2 mL of solution consisting of 50 mM HEPES buffer in 10%, 20%, 30%, or 40% methanol. This pre-exposure lasted from 0-240 minutes and was followed by the addition of the 10.8 mL of an assay solution containing a similar concentration of methanol and with the concentrations of HEPES, CoCl$_2$ and paraoxon adjusted so that at the final volume of 12 mL the solution would match the concentrations of the standard assay solutions previously tested.

The enzyme's specific activity (units/mg) was studied in methanol/water solutions (10%-40%) and the results are provided in Table 10, below. Time indicates how long enzyme material was exposed to solvent before assay was run. For each enzyme material the change is reverenced to the values at 10% methanol at 0 minutes of exposure.

TABLE 10

|  | % Methanol | 0 min | 60 min | 120 min | 180 min | 240 min |
|---|---|---|---|---|---|---|
| Enzyme/ | 10 | 0.0% | 8.1% | 0.9% | 7.1% | 1.6% |
| Cell | 20 | −57.8% | −60.5% | −69.1% | −68.8% | −67.0% |
| Slurry | 30 | −95.1% | −93.4% | −95.7% | −94.8% | −93.9% |
|  | 40 | −98.0% | −98.1% | −97.6% | −97.6% | −97.9% |
| OPH-7 | 10 | 0.0% | −3.2% | 19.5% | 15.7% | 22.0% |
|  | 20 | −28.9% | −44.6% | −34.5% | −42.3% | −44.8% |
|  | 30 | −52.4% | −65.4% | −68.1% | −70.3% | −73.5% |
|  | 40 | −85.8% | −95.9% | −96.9% | −97.3% | −98.5% |

From the data, the immobilized enzyme retains more activity over time with exposure to methanol. Additionally the methanol seems to increase the activity of the immobilized enzyme at the lowest tested concentration. The charts shown in FIGS. 10-17 further illustrate that while the enzyme activity is reduced by the increased presence of methanol (MeOH), there are only slight changes with respect to the amount of time the enzyme is exposed to higher amounts of methanol solution for both immobilized and whole cell OPH until the solution contains 30% or more MeOH. At this level a notable difference between immobilized samples exposed to the solution for more than an hour as compared to samples with no pre-exposure. Even with this decline in activity, the immobilized material still appears to outperform the whole cells at similar MeOH concentrations as indicated by the degree of change in absorbance vs. time. As noted in other testing, the process of immobilizing the OPH containing cells gives the enzyme an increased resistance to the deactivating effects of higher methanol concentrations in the assay solution.

Ethylene Glycol-Water Solution Stability

The enzyme's specific activity (units/mg) was studied in ethylene glycol-water solutions (10%-40% solvent), and the results are provided in Table 11, below. Time indicates how long enzyme material was exposed to solvent before assay was run. The listed change in activity in the table is referenced to the activity for that particular enzyme form in a 10% ethylene glycol solution at zero minutes.

TABLE 11

|  | % Ethylene Glycol | 0 min | 60 min | 120 min | 180 min | 240 min |
|---|---|---|---|---|---|---|
| Free | 10 | 0.0% | 1.5% | 0.9% | 6.3% | 5.2% |
| Enzyme/ | 20 | −68.1% | −62.5% | −57.4% | −69.0% | −60.7% |
| cell | 30 | −67.0% | −55.3% | −55.6% | −59.9% | −47.7% |
| Slurry | 40 | −91.5% | −87.3% | −84.6% | −80.9% | −79.9% |
| OPH-7 | 10 | 0.0% | 29.0% | 49.9% | 38.2% | 50.2% |
|  | 20 | −80.2% | −53.6% | −68.7% | −71.3% | −66.2% |
|  | 30 | −60.2% | −72.8% | −46.3% | −51.3% | −43.0% |
|  | 40 | −71.3% | −55.9% | −70.3% | −47.2% | −46.5% |
| OPH-14 | 10 | 0.0% | 28.8% | 77.5% | 96.9% | 84.2% |
|  | 20 | −72.5% | −73.7% | −62.5% | −65.4% | −60.2% |
|  | 30 | −48.1% | −53.7% | −59.5% | −53.2% | −59.4% |
|  | 40 | −58.4% | −68.5% | −64.4% | −72.4% | −67.6% |
| OPH-15 | 10 | 0.0% | 0.0% | 49.8% | 71.2% | 100.5% |
|  | 20 | −74.0% | −80.7% | −70.4% | −68.0% | −66.1% |
|  | 30 | −64.4% | −61.0% | −60.4% | −63.5% | −62.3% |
|  | 40 | −85.2% | −75.9% | −76.4% | −65.8% | −68.0% |

As with the isopropanol and methanol solution testing, the immobilized forms of the enzyme appear to grant increased stability or resistance to the denaturing properties of the solvent solution as compared to the free enzyme. In some cases it appears that the immobilized forms undergo a transformation upon exposure to the solvent that increases the enzyme activity as illustrated in FIGS. 18-21 which show the enzymatic activity relative for each enzyme form relative to its activity in solvent-free solutions.

Additional Solvents

The study of the enzyme's specific activity (units/mg) was expanded to include an additional aqueous solvent (DMSO) and to non-aqueous solvents (cyclohexane and toluene) in solution mixtures of 10%, 40%, 90%. The performance proportional to the enzyme form in solvent free solutions is provided in Table 12, below.

TABLE 12

| | | Solvent % | | |
|---|---|---|---|---|
| Sample | Solvent | 10% | 40% | 90% |
| Free Enzyme/Cell Slurry | toluene | −72.3% | −55.3% | −87.4% |
| OPH-7 | toluene | −34.8% | −54.4% | −1.1% |
| OPH-16B | toluene | −52.2% | −72.9% | −30.2% |
| Free Enzyme/Cell Slurry | cyclohexane | −1.6% | −69.8% | −82.3% |
| OPH-7 | cyclohexane | 90.2% | 15.5% | −16.0% |
| OPH-16B | cyclohexane | 28.1% | −70.8% | −85.4% |
| Free Enzyme/Cell Slurry | dimethyl sulfoxide | −96.8% | −97.9% | −99.7% |
| OPH-7 | dimethyl sulfoxide | 87.9% | −56.9% | −92.3% |
| OPH-16B | dimethyl sulfoxide | −6.0% | −77.2% | −97.2% |

In general the immobilized forms perform better than the free enzyme in solutions containing these solvents. In a similar fashion to the previously tested solvents there appears to be some cases where the immobilized enzyme activity increase with exposure to the solvent.

The Effect of pH

Related Studies at pH's Ranging from about 4.0 to 10.0

The enzyme's specific activity (units/mg) was studied (both as the free enzyme and in the form of 200 μm particles) across a pH range of 4-10. The results, compared as the change in activity from standard assay conditions (pH 7.5), are provided in Table 13, below. Although the activity is poor, the immobilized material does retain more activity in slightly acidic pH conditions (pH 5-6) compared to the free enzyme. The change in the activity of the immobilized enzyme is dependent on the formulation and process of immobilization, further exemplified by comparing the change in specific activity (units/mg) with a shift of one pH unit in Table 14.

TABLE 13

| pH | Enzyme/Cell Slurry | OPH-6 | OPH-7 | OPH-14 |
|---|---|---|---|---|
| 10 | 44.4% | −34.2% | 53.3% | 68.6% |
| 9.5 | 58.1% | −62.2% | 147.2% | 108.8% |
| 9 | 82.8% | −25.3% | 78.3% | 110.1% |
| 8.5 | 76.1% | −40.3% | 90.8% | 64.7% |
| 8 | 84.0% | −32.2% | 89.1% | 73.9% |
| 7.5 | 0.0% | 0.0% | 0.0% | 0.0% |
| 7 | −33.0% | −78.2% | −18.3% | −50.4% |
| 6 | −97.0% | −77.9% | −80.3% | −81.8% |
| 5 | −99.3% | −55.9% | −93.8% | −96.5% |
| 4 | −99.6% | −98.8% | −97.9% | −91.9% |

TABLE 14

| | OPH-10A | OPH-10B | OPH-11A | OPH-11B | OPH-16A | OPH-16B |
|---|---|---|---|---|---|---|
| pH 7.5 | 5.1 | 5.7 | 6.0 | 2.9 | 5.8 | 6.9 |
| pH 8.5 | 3.7 | 5.5 | 20.7 | 5.7 | 6.8 | 11.4 |
| % Change | −27.4% | −4.6% | 244.2% | 100.9% | 16.8% | 64.7% |

While the disclosed technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the disclosed technology are desired to be protected.

What is claimed is:

1. An immobilized enzyme material comprising a crosslinked enzyme having a support matrix that includes a biomass material different from the biomass material the enzyme was derived from, wherein the crosslinked enzyme was formed by reacting the enzyme with at least two polyfunctional materials, the immobilized enzyme material has a particulate form, the biomass material included in the support matrix has not been chemically processed prior to reacting the enzyme with the at least two polyfunctional materials and the immobilized enzyme material exhibits enzymatic activity.

2. The immobilized enzyme material of claim 1, wherein the biomass material different from the biomass material the enzyme was derived from is insoluble.

3. The immobilized enzyme material of claim 1, wherein at least one of the two polyfunctional materials is selected from the group consisting of a di-aldehyde, disuccinimidyl suberate, an organic di-acid, glutaraldehyde, dimethyl pimelimidate, cyanuric chloride, succinic acid, hexamethylene diisocyanate, diimidoester, triazine, diisocyanate, and di(n-hydroxysuccinimide ester).

4. The immobilized enzyme material of claim 1, wherein at least one of the two polyfunctional materials is a polyamine.

5. The immobilized enzyme material of claim 4, wherein at least one of the two polyfunctional materials which is a polyamine is selected from the group consisting of polyethylenimine, polypyrrole, chitosan, a protein, and gelatin.

6. The immobilized enzyme material of claim 1, wherein the biomass material different from the biomass material the enzyme was derived from is selected from the group consisting of bacterial cell material, fungal cell material, cellulose, collagen, cotton, chitin, exoskeleton, and wool.

7. The immobilized enzyme material of claim 1, wherein the immobilized enzyme material is biodegradable.

8. The immobilized enzyme material of claim 1, wherein the enzyme belongs to a class selected from the group consisting of Oxidoreductases, Transferases, Hydrolases, Lyases, Isomerases, and Ligases.

9. The immobilized enzyme material of claim 1, wherein the immobilized enzyme material further includes biomass material from which the enzyme was derived.

10. The immobilized enzyme material of claim 1, wherein at least one of the two polyfunctional materials includes biomass material having a plurality of amine groups thereon.

11. The immobilized enzyme material of claim 10, wherein the at least one polyfunctional material which includes a biomass material is selected from the group consisting of bacterial cell material, fungal cell material, collagen, chitin, exoskeleton, and wool.

12. A method for preparing an immobilized enzyme material comprising:
providing an aqueous suspension of an enzyme, a biomass material that has not been chemically processed and which is different than the biomass from which the enzyme was derived, and at least two polyfunctional materials;
adding the biomass material, and one of the two polyfunctional materials to the aqueous suspension of the enzyme to form a reaction mixture;

adding the second polyfunctional material to the reaction mixture to flocculate the immobilized enzyme material; and obtaining a crosslinked immobilized enzyme material having a support matrix that includes the biomass material, having a particulate form and exhibiting enzymatic activity.

13. The method of claim 12, wherein the method further involves stirring the reaction mixture before adding the second polyfunctional material to the reaction mixture.

14. The method of claim 12, wherein providing a biomass material and the at least two polyfunctional materials, involves providing a biodegradable biomass material and biodegradable polyfunctional materials.

15. The method of claim 12, wherein providing a biomass material involves providing a biomass material that is insoluble.

16. The method of claim 12, wherein providing a biomass material involves providing a biomass material is selected from the group consisting of bacterial cell material, fungal cell material, cellulose, cotton, chitin, exoskeleton, and wool.

17. The method of claim 12, wherein providing an aqueous suspension of an enzyme involves providing an aqueous suspension of an enzyme which belongs to a class selected from the group consisting of Oxidoreductases, Transferases, Hydrolases, Lyases, Isomerases, and Ligases.

18. The method of claim 12, wherein providing at least two polyfunctional materials involves providing an additional biomass material having a plurality of amine groups thereon.

19. The method of claim 18, wherein the additional biomass material is selected from the group consisting of bacterial cell material, fungal cell material, cellulose, dextran, starch agar, alginate, carrageenans, collagen, gelatin, albumin, ferritin, cotton, chitin, exoskeleton, and wool.

20. The method of claim 12, wherein at least one of the two polyfunctional materials is selected from the group consisting of a di-aldehyde, disuccinimidyl suberate, an organic di-acid, glutaraldehyde, dimethyl pimelimidate, cyanuric chloride, succinic acid, hexamethylene diisocyanate, diimidoester, triazine, diisocyanate, and di(n-hydroxysuccinimide ester).

21. The method of claim 12, wherein providing at least two polyfunctional materials involves providing a polyamine selected from the group consisting of polyethylenimine, polypyrrole, chitosan, a protein, and gelatin.

22. The method of claim 12, wherein the provided enzyme is an organophosphate-degrading enzyme.

23. The method of claim 12, wherein the immobilized enzyme material further includes biomass material from which the enzyme was derived.

24. The method of claim 12, wherein at least one of the two polyfunctional materials is a polyamine.

25. A method for decontaminating an area containing a material susceptible to enzymatic degradation comprising:

providing a biodegradable immobilized enzyme material in a form suitable for application to an area and adapted to degrade the material;

contacting the area with the form of the biodegradable immobilized enzyme material;

wherein:

(a) the biodegradable immobilized enzyme material is a crosslinked enzyme having a support matrix that includes a biomass material different from the biomass material the enzyme was derived from;

(b) the crosslinked enzyme was formed by reacting the enzyme with at least two polyfunctional materials;

(c) the immobilized enzyme material has a particulate form;

(d) the biomass material included in the support matrix has not been chemically processed prior to reacting the enzyme with the at least two polyfunctional materials;

(e) the immobilized enzyme material exhibits enzymatic activity; and (f) upon degradation of the material, the biodegradable immobilized enzyme material itself biodegrades, making its removal unnecessary.

26. A method for transforming a material susceptible to enzymatic transformation comprising:

providing a biodegradable immobilized enzyme material adapted to transform the material in a form suitable for use in a reaction chamber;

placing the immobilized enzyme material in a reaction chamber;

contacting the material to be transformed with the immobilized enzyme material in the reaction chamber;

removing the immobilized enzyme material from the reaction chamber to an area where the immobilized enzyme material may biodegrade wherein:

(a) the biodegradable immobilized enzyme material is a crosslinked enzyme having a support matrix that includes a biomass material different from the biomass material the enzyme was derived from;

(b) the crosslinked enzyme was formed by reacting the enzyme with at least two polyfunctional materials;

(c) the immobilized enzyme material has a particulate form;

(d) the biomass material included in the support matrix has not been chemically processed prior to crosslinking the enzyme; and (e) the immobilized enzyme material exhibits enzymatic activity.

27. The method of claim 26, wherein the reaction chamber is a reaction column.

28. The method of claim 26, wherein the reaction chamber is a closed reaction vessel.

29. The method of claim 26, wherein the reaction chamber is a packed bed.

* * * * *